(12) United States Patent (10) Patent No.: US 8,962,889 B2
Hayashi (45) Date of Patent: Feb. 24, 2015

(54) PROCESS FOR PRODUCING OPTICALLY ACTIVE β-AMINO ALDEHYDE COMPOUND

(75) Inventor: Yujiro Hayashi, Sendai (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/880,675

(22) PCT Filed: Oct. 9, 2011

(86) PCT No.: PCT/JP2011/074073
§ 371 (c)(1),
(2), (4) Date: Apr. 19, 2013

(87) PCT Pub. No.: WO2012/053565
PCT Pub. Date: Apr. 26, 2012

(65) Prior Publication Data
US 2013/0211139 A1 Aug. 15, 2013

(30) Foreign Application Priority Data
Oct. 20, 2010 (JP) ................................ 2010-235793

(51) Int. Cl.
*C07C 251/12* (2006.01)
*C07C 311/06* (2006.01)
*C07C 303/40* (2006.01)
*C07B 53/00* (2006.01)

(52) U.S. Cl.
CPC ............... *C07C 303/40* (2013.01); *C07B 53/00* (2013.01); *C07C 2101/14* (2013.01); *C07B 2200/07* (2013.01)
USPC .............................. 564/278; 564/248; 564/90

(58) Field of Classification Search
CPC ...... C07C 311/16; C07C 303/40; C07B 53/00
USPC ...................... 564/30, 90, 248, 278
See application file for complete search history.

(56) References Cited

U.S. PATENT DOCUMENTS 5,053,548 A 10/1991 Tanaka et al.

FOREIGN PATENT DOCUMENTS

JP H04-154737 A 5/1992
JP 2007-182419 A 7/2007
JP 2010-047490 A 3/2010

OTHER PUBLICATIONS

Gianelli et al., "Aminocatalytic Enantioselective anti-Mannich Reaction of Aldehydes with in Situ Generated N-Cbz and N-Boc Imines," Angew. CHem. Int. Ed., 2008, 47, 8700-8702.*
Amedjkouh et al. "Asymmetric autocatalytic Mannich reaction in the presence of water and its implication in prebiotic chemistry," Chem. Comm., 2008, 3043-3045.*
Verkade et al., "Organocatalysed Asymmetric Mannich Reactions," Chem. Soc. Rev., 37, 29-41, 2008.*
Yang et al., "Proline-catalysed Mannich reactions of acetaldehyde," Nature, 452(27), Mar. 2008, 453-455.*
Hayashi, *Journal of Synthetic Organic Chemistry*, Japan, 63 (5): 464-477 (2005).
Hayashi et al., *CSJ: The Chemical Society of Japan Koen Yokoshu*, 85(2): 1048, abstract 1 C1-11 (2005).
Hayashi et al., *Angewandte Chemie International Edition*, 47: 9053-9058 (2008).
Urushima et al., *Chemistry European Journal*, 17: 8273-8276 (2011).
Yang et al., *Angewandte Chemie International Edition*, 46: 609-611 (2007).
Japanese Patent Office, International Search Report in International Patent Application No. PCT/JP2011/074073 (Dec. 13, 2011).

* cited by examiner

*Primary Examiner* — Paul A Zucker
*Assistant Examiner* — Mark Luderer
(74) *Attorney, Agent, or Firm* — Leydig, Voit & Mayer, Ltd.

(57) ABSTRACT

The invention relates to a method of producing optically active β-aminoaldehyde compound (3) by reacting imine compound (1-1) or sulfone compound (1-2) with aldehyde compound (2) in the presence of an optically active pyrrolidine compound.

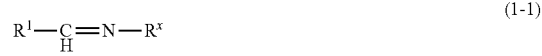
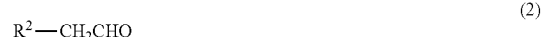
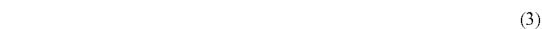

wherein each symbol is as defined in the specification.

9 Claims, No Drawings

PROCESS FOR PRODUCING OPTICALLY ACTIVE β-AMINO ALDEHYDE COMPOUND

CROSS-REFERENCE TO RELATED APPLICATIONS

This patent application is the U.S. national phase of International Patent Application No. PCT/JP2011/074073, filed on Oct. 19, 2011, which claims the benefit of Japanese Patent Application No. 2010-235793, filed Oct. 20, 2010, which are incorporated by reference in their entireties herein.

TECHNICAL FIELD

The present invention relates to a production method of an optically active β-aminoaldehyde compound.

BACKGROUND ART

An optically active β-aminoaldehyde compound is known to be useful for as an intermediate for producing, for example, a therapeutic drug for diabetes and a therapeutic drug for Alzheimer's disease.

Concerning a production method of an optically active β-aminoaldehyde compound, for example, non-patent document 1 discloses that β-amino-β-phenylpropanal can be obtained by reacting an aromatic imine compound with an aldehyde compound in the presence of (S)-proline. Non-patent document 1 also discloses that the objective optically active β-aminoaldehyde compound cannot be obtained by replacing the aromatic imine compound with an aliphatic imine in the above-mentioned method.

DOCUMENT LIST

Non-Patent Document

Non-Patent Document 1: Angewandte Chemie International Edition, vol. 46, pages 609-611, 2007

SUMMARY OF THE INVENTION

Problems to be Solved by the Invention

The aim of the present invention is to provide a new method capable of producing an optically active β-aminoaldehyde compound from an imine compound.

Means of Solving the Problems

Under the circumstances, the present inventors have studied a new production method of an optically active β-aminoaldehyde compound, and found that by a reaction in the presence of a particular asymmetric catalyst, an optically active β-aminoaldehyde compound can be produced from an imine compound, which resulted in the completion of the present invention. Accordingly, the present invention is as follows.

[1] A method of producing an optically active compound represented by the formula (3):

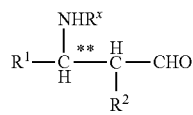

(3)

wherein
$R^1$ is a $C_1$-$C_{20}$ hydrocarbon group optionally having substituent(s) selected from the following Group G1 or a hydrogen atom,
$R^2$ is a $C_1$-$C_{20}$ hydrocarbon group optionally having substituent(s) selected from the following Group G1, a $C_1$-$C_{12}$ alkoxy group optionally having substituent(s) selected from the following Group G1, a $C_1$-$C_{12}$ alkylthio group optionally having substituent(s) selected from the following Group G1, a protected amino group, a heterocyclic group optionally having substituent(s) selected from the following Group G2 or a hydrogen atom,
$R^X$ is an amino-protecting group, and the carbon atom marked with ** is an asymmetric carbon atom (hereinafter referred to as optically active β-aminoaldehyde compound (3)), which comprises a step of reacting a compound represented by the formula (1-1):

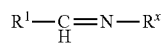

(1-1)

wherein
$R^1$ and $R^X$ are as defined above (hereinafter referred to as imine compound (1-1)), or a compound represented by the formula (1-2):

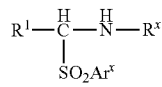

(1-2)

wherein
$R^1$ and $R^X$ are as defined above, and
$Ar^X$ is a phenyl group optionally having substituent(s) selected from the following Group G2
(hereinafter referred to as sulfone compound (1-2)) with a compound represented by the formula (2):

(2)

wherein
$R^2$ is as defined above
(hereinafter referred to as aldehyde compound (2)), in the presence of an optically active compound represented by the formula (4):

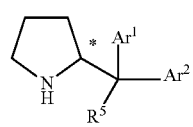

(4)

wherein
$Ar^1$ and $Ar^2$ are each independently a phenyl group optionally having substituent(s) selected from the following Group G2, a $C_1$-$C_{12}$ chain hydrocarbon group, a $C_3$-$C_{12}$ alicyclic hydrocarbon group or a hydrogen atom,
$R^5$ is a hydrogen atom, a fluorine atom, a hydroxyl group, a $C_1$-$C_{12}$ alkoxy group, a $C_1$-$C_{12}$ fluorinated alkyloxy group or a group represented by —$OSiR^6R^7R^8$ wherein $R^6$, $R^7$ and $R^8$ are each independently a $C_1$-$C_8$ alkyl group or a $C_6$-$C_{20}$ aryl group, and the carbon atom marked with * is an asymmetric carbon atom (hereinafter referred to as optically active pyrrolidine compound (4));
<Group G1>: a group consisting of a $C_6$-$C_{20}$ aryl group optionally having substituent(s) selected from Group G2, an aromatic heterocyclic group optionally having substituent(s) selected from Group G2, a $C_1$-$C_{12}$ alkyl group, a $C_1$-$C_{12}$ alkoxy group, a $C_1$-$C_{12}$ alkyl group having $C_8$-$C_{20}$ aryl group(s) optionally having substituent(s) selected from Group G2, a $C_1$-$C_{12}$ alkoxy group having $C_6$-$C_{20}$ aryl group(s) optionally having substituent(s) selected from Group G2, a halogen atom, a $C_2$-$C_{13}$ alkylcarbonyl group, a $C_2$-$C_{13}$ alkoxycarbonyl group, a $C_1$-$C_{12}$ fluorinated alkyl group, a $C_1$-$C_{12}$ fluorinated alkyloxy group, a $C_2$-$C_{13}$ acyl group, a nitro group, a cyano group, a protected amino group and an oxo group
<Group G2>: a group consisting of a $C_1$-$C_{12}$ alkyl group, a $C_1$-$C_{12}$ alkoxy group, a $C_2$-$C_{13}$ alkylcarbonyl group, a $C_2$-$C_{13}$ alkoxycarbonyl group, a $C_1$-$C_{12}$ fluorinated alkyl group, a $C_1$-$C_{12}$ fluorinated alkyloxy group, a $C_2$-$C_{13}$ acyl group, a nitro group, a cyano group, a protected amino group and a halogen atom
[2] The method of the above-mentioned [1], wherein the reaction is carried out in a solvent.
[3] The method of the above-mentioned [2], wherein the solvent is water.
[4] The method of the above-mentioned [2], wherein the solvent is water containing an inorganic salt.
[5] The method of the above-mentioned [4], wherein the inorganic salt is sodium chloride.
[6] The method of the above-mentioned [2], wherein the solvent is an ether solvent.
[7] The method of the above-mentioned [1], wherein $R^5$ is a group represented by —$OSiR^6R^7R^8$ wherein each symbol is as defined in the above-mentioned [1], and $Ar^1$ and $Ar^2$ are each independently a phenyl group having $C_1$-$C_{12}$ fluorinated alkyl group(s).

Effect of the Invention

The production method of the present invention can provide a new method capable of producing an optically active β-aminoaldehyde compound from an imine compound.

In addition, by using optically active pyrrolidine compound (4) having a particular structure, optically active β-aminoaldehyde compound (3) can be produced in good yield, superior enantioselectivity and diastereoselectivity (when $R^2$ in aldehyde compound (2) is not a hydrogen atom).

DESCRIPTION OF EMBODIMENTS

The present invention is explained in detail below.
In the present specification, the "halogen atom" means a fluorine atom, a chlorine atom, a bromine atom or an iodine atom.
In the present specification, the "$C_1$-$C_{20}$ hydrocarbon group" means a $C_1$-$C_{20}$ aliphatic hydrocarbon group or a $C_6$-$C_{20}$ aromatic hydrocarbon group.
In the present specification, the "$C_1$-$C_{20}$ aliphatic hydrocarbon group" means a $C_1$-$C_{20}$ chain hydrocarbon group or a $C_3$-$C_{20}$ alicyclic hydrocarbon group.

In the present specification, the "$C_1$-$C_{12}$ aliphatic hydrocarbon group" means a $C_1$-$C_{12}$ chain hydrocarbon group or a $C_3$-$C_{12}$ alicyclic hydrocarbon group.
In the present specification, the "$C_1$-$C_{20}$ chain hydrocarbon group" means a $C_1$-$C_{20}$ alkyl group, a $C_2$-$C_{20}$ alkenyl group or a $C_2$-$C_{20}$ alkynyl group.
In the present specification, the "$C_1$-$C_{12}$ chain hydrocarbon group" means a $C_1$-$C_{12}$ alkyl group, a $C_2$-$C_{12}$ alkenyl group or a $C_2$-$C_{12}$ alkynyl group.
In the present specification, the "$C_1$-$C_{20}$ alkyl group" means a straight or branched chain alkyl group having 1 to 20 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl, tridecyl, eicosyl and the like. Among them, a $C_1$-$C_{12}$ alkyl group is preferable, and a $C_1$-$C_8$ alkyl group is particularly preferable.
In the present specification, the "$C_1$-$C_{12}$ alkyl group" means a straight or branched chain alkyl group having 1 to 12 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl and the like. Among them, a $C_1$-$C_8$ alkyl group is preferable, and a $C_1$-$C_4$ alkyl group is particularly preferable.
In the present specification, the "$C_1$-$C_8$ alkyl group" means a straight or branched chain alkyl group having 1 to 8 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl and the like. Among them, a $C_1$-$C_4$ alkyl group is preferable.
In the present specification, the "$C_1$-$C_6$ alkyl group" means a straight or branched chain alkyl group having 1 to 6 carbon atoms, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like. Among them, a $C_1$-$C_4$ alkyl group is preferable.
In the present specification, the "$C_1$-$C_4$ alkyl group" means a straight or branched chain alkyl group having 1 to 4 carbon atoms, and examples thereof include methyl, ethyl, propyl, isopropyl, butyl, isobutyl, sec-butyl, tert-butyl and the like.
In the present specification, the "$C_2$-$C_{20}$ alkenyl group" means a straight or branched chain alkenyl group having 2 to 20 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl, 1-nonenyl, 1-decenyl, 1-undecenyl, 1-dodecenyl, 1-tridecenyl, 1-eicosenyl and the like. Among them, a $C_2$-$C_{12}$ alkenyl group is preferable, and a $C_2$-$C_8$ alkenyl group is particularly preferable.
In the present specification, the "$C_2$-$C_{12}$ alkenyl group" means a straight or branched chain alkenyl group having 2 to 12 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl, 1-nonenyl, 1-decenyl, 1-undecenyl, 1-dodecenyl and the like. Among them, a $C_2$-$C_8$ alkenyl group is preferable, and a $C_2$-$C_4$ alkenyl group is particularly preferable.

In the present specification, the "$C_2$-$C_6$ alkenyl group" means a straight or branched chain alkenyl group having 2 to 6 carbon atoms, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like. Among them, a $C_2$-$C_4$ alkenyl group is particularly preferable.

In the present specification, the "$C_2$-$C_{20}$ alkynyl group" means a straight or branched chain alkynyl group having 2 to 20 carbon atoms, and examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl, 1-undecynyl, 1-dodecynyl, 1-tridecynyl, 1-eicosynyl and the like. Among them, a $C_2$-$C_{12}$ alkynyl group is preferable, and a $C_2$-$C_8$ alkynyl group is particularly preferable.

In the present specification, the "$C_2$-$C_{12}$ alkynyl group" means a straight or branched chain alkynyl group having 2 to 12 carbon atoms, and examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, 1-nonynyl, 1-decynyl, 1-undecynyl, 1-dodecynyl and the like. Among them, a $C_2$-$C_8$ alkynyl group is preferable, and a $C_2$-$C_4$ alkynyl group is particularly preferable.

In the present specification, the "$C_2$-$C_6$ alkynyl group" means a straight or branched chain alkynyl group having 2 to 6 carbon atoms, and examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_2$-$C_4$ alkynyl group is preferable.

In the present specification, the "$C_3$-$C_{20}$ alicyclic hydrocarbon group" means a $C_3$-$C_{20}$ cycloalkyl group or a $C_4$-$C_{20}$ cycloalkenyl group.

In the present specification, the "$C_3$-$C_{12}$ alicyclic hydrocarbon group" means a $C_3$-$C_{12}$ cycloalkyl group or a $C_4$-$C_{12}$ cycloalkenyl group.

In the present specification, the "$C_3$-$C_{20}$ cycloalkyl group" means a cyclic alkyl group having 3 to 20 carbon atoms, and examples thereof include cyclopropyl, cyclobutyl, cyclopentyl, cyclohexyl, cycloheptyl, cyclooctyl, cyclononyl, cyclodecyl, cycloundecyl, cyclododecyl, cyclotridecyl, cycloeicosyl and the like. Among them, a $C_3$-$C_{12}$ cycloalkyl group is preferable, and a $C_3$-$C_8$ cycloalkyl group is particularly preferable.

In the present specification, the "$C_3$-$C_{12}$ cycloalkyl group" means a cyclic alkyl group having 3 to 12 carbon atoms, and examples thereof include cyclopropyl, cyclobutyl, cyclopentyl, cyclohexyl, cycloheptyl, cyclooctyl, cyclononyl, cyclodecyl, cycloundecyl, cyclododecyl and the like. Among them, a $C_3$-$C_8$ cycloalkyl group is preferable.

In the present specification, the "$C_4$-$C_{20}$ cycloalkenyl group" means a cyclic alkenyl group having 4 to 20 carbon atoms, and examples thereof include 2-cyclopenten-1-yl, 3-cyclopenten-1-yl, 2-cyclohexen-1-yl, 3-cyclohexen-1-yl, 2-cyclohepten-1-yl, 2-cycloocten-1-yl, 2-cyclononen-1-yl, 2-cyclodecen-1-yl, 2-cyclododecen-1-yl, 2-cycloeicosen-1-yl, 2,4-cyclopentadien-1-yl, 2,4-cyclohexadien-1-yl, 2,5-cyclohexadien-1-yl and the like. Among them, a $C_4$-$C_{12}$ cycloalkenyl group is preferable, and a $C_4$-$C_8$ cycloalkenyl group is particularly preferable.

In the present specification, the "$C_4$-$C_{12}$ cycloalkenyl group" means a cyclic alkenyl group having 4 to 12 carbon atoms, and examples thereof include 2-cyclopenten-1-yl, 3-cyclopenten-1-yl, 2-cyclohexen-1-yl, 3-cyclohexen-1-yl, 2-cyclohepten-1-yl, 2-cycloocten-1-yl, 2-cyclononen-1-yl, 2-cyclodecen-1-yl, 2-cyclododecen-1-yl, 2,4-cyclopentadien-1-yl, 2,4-cyclohexadien-1-yl, 2,5-cyclohexadien-1-yl and the like. Among them, a $C_4$-$C_8$ cycloalkenyl group is preferable.

In the present specification, the "$C_3$-$C_{20}$ cycloalkyl group", "$C_3$-$C_{12}$ cycloalkyl group", "$C_4$-$C_{20}$ cycloalkenyl group" and "$C_4$-$C_{12}$ cycloalkenyl group" are optionally fused with a benzene ring, and examples thereof include 1,2-dihydronaphthalen-1-yl, 1,2-dihydronaphthalen-2-yl, 1,2,3,4-tetrahydronaphthalen-1-yl, 1,2,3,4-tetrahydronaphthalen-2-yl, fluoren-9-yl, inden-1-yl and the like.

In the present specification, the "$C_6$-$C_{20}$ aromatic hydrocarbon group (the $C_6$-$C_{20}$ aryl group)" means a monocyclic or polycyclic (fused) hydrocarbon group having 6 to 20 carbon atoms and showing aromaticity, and examples thereof include phenyl, 1-naphthyl, 2-naphthyl, phenanthryl, anthryl, acenaphthyl, naphthacenyl, biphenylyl and the like. Among them, a $C_6$-$C_{14}$ aromatic hydrocarbon group (a $C_6$-$C_{14}$ aryl group) is preferable, and a $C_6$-$C_{10}$ aromatic hydrocarbon group (a $C_6$-$C_{10}$ aryl group) is particularly preferable.

In the present specification, the "$C_6$-$C_{12}$ aromatic hydrocarbon group (the $C_6$-$C_{12}$ aryl group)" means a monocyclic or polycyclic (fused) hydrocarbon group having 6 to 12 carbon atoms and showing aromaticity, and examples thereof include phenyl, 1-naphthyl, 2-naphthyl, acenaphthyl, biphenylyl and the like. Among them, a $C_6$-$C_{10}$ aromatic hydrocarbon group (a $C_6$-$C_{10}$ aryl group) is preferable.

In the present specification, the "$C_6$-$C_{10}$ aryl group" means a monocyclic or polycyclic (fused) hydrocarbon group having 6 to 10 carbon atoms and showing aromaticity, and examples thereof include phenyl, 1-naphthyl, 2-naphthyl and the like.

In the present specification, the "$C_7$-$C_{14}$ aralkyl group" means a alkyl "$C_{1-4}$ group" substituted by "$C_6$-$C_{10}$ aryl group(s)", and examples thereof include benzyl, 1-phenylethyl, 2-phenylethyl, (naphthyl-1-yl)methyl, (naphthyl-2-yl)methyl, 1-(naphthyl-1-yl)ethyl, 1-(naphthyl-2-yl)ethyl, 2-(naphthyl-1-yl)ethyl, 2-(naphthyl-2-yl)ethyl and the like.

In the present specification, the "$C_1$-$C_{12}$ alkoxy group" means a straight or branched chain alkoxy group having 1 to 12 carbon atoms, and examples thereof include methoxy, ethoxy, propoxy, isopropoxy, butoxy, isobutoxy, sec-butoxy, tert-butoxy, pentyloxy, isopentyloxy, neopentyloxy, hexyloxy, heptyloxy, octyloxy, nonyloxy, decyloxy, undecyloxy, dodecyloxy and the like. Among them, a $C_1$-$C_8$ alkoxy group is preferable, and a $C_1$-$C_4$ alkoxy group is particularly preferable.

In the present specification, the "$C_1$-$C_6$ alkoxy group" means a straight or branched chain alkoxy group having 1 to 6 carbon atoms, and examples thereof include methoxy, ethoxy, propoxy, isopropoxy, butoxy, isobutoxy, sec-butoxy, tert-butoxy, pentyloxy, isopentyloxy, neopentyloxy, hexyloxy and the like. Among them, a $C_1$-$C_4$ alkoxy group is preferable.

In the present specification, the "$C_1$-$C_{12}$ alkylthio group" means a straight or branched chain alkylthio group having 1 to 12 carbon atoms, and examples thereof include methylthio, ethylthio, propylthio, isopropylthio, butylthio, isobutylthio, sec-butylthio, tert-butylthio, pentylthio, isopentylthio, neopentylthio, hexylthio, heptylthio, octylthio, nonylthio, decylthio, undecylthio, dodecylthio and the like. Among them a C$_1$-C$_8$ alkylthio group is preferable, and a C$_1$-C$_4$ alkylthio group is particularly preferable.

In the present specification, the "aromatic heterocyclic group" means a monocyclic or polycyclic (fused) heterocyclic group containing, as a ring-constituting atom besides carbon atom, 1 to 4 hetero atoms selected from an oxygen atom, a sulfur atom and a nitrogen atom, and showing aromaticity.

In the present specification, examples of the "monocyclic aromatic heterocyclic group" include furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl (1,2,4-oxadiazolyl, 1,3,4-oxadiazolyl), thiadiazolyl (1,2,4-thiadiazolyl, 1,3,4-thiadiazolyl), triazolyl (1,2,4-triazolyl, 1,2,3-triazolyl), tetrazolyl, triazinyl and the like. Among them, a 5- or 6-membered monocyclic aromatic heterocyclic group is preferable.

In the present specification, the "fused aromatic heterocyclic group" means the above-mentioned monocyclic aromatic heterocyclic group fused with a monocyclic aromatic ring (preferably a benzene ring or a monocyclic aromatic heterocycle), and examples thereof include quinolyl, isoquinolyl, quinazolyl, quinoxalyl, benzofuranyl, benzothienyl, benzoxazolyl, benzisoxazolyl, benzothiazolyl, benzisothiazolyl, benzimidazolyl, benzotriazolyl, indolyl, indazolyl, pyrrolopyridyl, pyrazolopyridyl, imidazopyridyl, thienopyridyl, pyrrolopyrazinyl, pyrazolopyrazinyl, imidazopyrazinyl, thienopyrazinyl, pyrrolopyrimidinyl, pyrazolopyrimidinyl, imidazopyrimidinyl, thienopyrimidinyl, pyrazolothienyl and the like.

In the present specification, examples of the "monocyclic aromatic heterocycle" include furan, thiophene, pyridine, pyrimidine, pyridazine, pyrazine, pyrrole, imidazole, pyrazole, thiazole, isothiazole, oxazole, isoxazole, oxadiazole (1,2,4-oxadiazole, 1,3,4-oxadiazole), thiadiazole (1,2,4-thiadiazole, 1,3,4-thiadiazole), triazole (1,2,4-triazole, 1,2,3-triazole), tetrazole, triazine and the like. Among them, a 5- or 6-membered monocyclic aromatic heterocycle is preferable.

In the present specification, the "C$_1$-C$_{12}$ fluorinated alkyl group" means a "C$_1$-C$_{12}$ alkyl group" substituted by fluorine atom(s). The number of the fluorine atoms is not particularly limited, and the C$_1$-C$_{12}$ fluorinated alkyl group may be perfluoro-substituted. Specific examples thereof include fluoromethyl, difluoromethyl, trifluoromethyl, 2-fluoroethyl, 2,2-difluoroethyl, 2,2,2-trifluoroethyl, 3-fluoropropyl, 4-fluorobutyl, 5-fluoropentyl, 6-fluorohexyl, 7-fluoroheptyl, 8-fluorooctyl, 9-fluorononyl, 10-fluorodecyl, 11-fluoroundecyl, 12-fluorododecyl and the like. Among them, a C$_1$-C$_6$ fluorinated alkyl group is preferable.

In the present specification, the "C$_1$-C$_{12}$ fluorinated alkyloxy group" means a "C$_{1-12}$ alkoxy group" substituted by fluorine atom(s). The number of the fluorine atoms is not particularly limited, and the C$_1$-C$_{12}$ fluorinated alkyloxy group may be perfluoro-substituted. Specific examples thereof include fluoromethoxy, difluoromethoxy, trifluoromethoxy, 2-fluoroethoxy, 2,2-difluoroethoxy, 2,2,2-trifluoroethoxy, 3-fluoropropoxy, 4-fluorobutoxy, 5-fluoropentyloxy, 6-fluorohexyloxy, 7-fluoroheptyloxy, 8-fluorooctyloxy, 9-fluorononyloxy, 10-fluorodecyloxy, 11-fluoroundecyloxy, 12-fluorododecyloxy and the like. Among them, a C$_1$-C$_6$ fluorinated alkyloxy group is preferable.

In the present specification, the "C$_2$-C$_{13}$ alkylcarbonyl group" means a group wherein a "C$_1$-C$_{12}$ alkyl group" is bonded to —C(=O)—, i.e., a "C$_1$-C$_{12}$ alkyl-carbonyl group", and examples thereof include methylcarbonyl, ethylcarbonyl, propylcarbonyl, isopropylcarbonyl, butylcarbonyl, isobutylcarbonyl, sec-butylcarbonyl, tert-butylcarbonyl, pentylcarbonyl, isopentylcarbonyl, neopentylcarbonyl, hexylcarbonyl, heptylcarbonyl, octylcarbonyl, nonylcarbonyl, decylcarbonyl, undecylcarbonyl, dodecylcarbonyl and the like. Among them a C$_2$-C$_9$ alkylcarbonyl group is preferable, and a C$_2$-C$_5$ alkylcarbonyl group is particularly preferable.

In the present specification, the "C$_2$-C$_{13}$ alkoxycarbonyl group" means a group wherein a "C$_1$-C$_{12}$ alkoxy group" is bonded to —C=O—, i.e., a "C$_1$-C$_{12}$ alkoxy-carbonyl group", and examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl and the like. Among them, a C$_2$-C$_9$ alkoxycarbonyl group is preferable, and a C$_2$-C$_5$ alkoxycarbonyl group is particularly preferable.

In the present specification, the "C$_2$-C$_{13}$ acyl group" is a residue obtained by removing a hydroxyl group from a C$_2$-C$_{13}$ carboxylic acid, and it means a "C$_2$-C$_{13}$ aliphatic acyl group" or a "C$_7$-C$_{13}$ aromatic acyl group".

In the present specification, the "C$_2$-C$_{13}$ aliphatic acyl group" means a group wherein a "C$_1$-C$_{12}$ aliphatic hydrocarbon group" is bonded to —C=O—, i.e., a "C$_1$-C$_{12}$ aliphatic hydrocarbon-carbonyl group", and examples thereof include acetyl, propanoyl, butanoyl, 2-methylpropanoyl, pentanoyl, hexanoyl, heptanoyl, octanoyl, nonanoyl, decanoyl, undecanoyl, dodecanoyl, acryloyl, methacryloyl, crotonoyl, isocrotonoyl, propionoyl, cyclopentylcarbonyl, cyclohexylcarbonyl and the like. Among them, a C$_2$-C$_{13}$ alkylcarbonyl group is preferable, and a C$_2$-C$_9$ alkylcarbonyl group is particularly preferable.

In the present specification, the "C$_7$-C$_{13}$ aromatic acyl group" means a group wherein a "C$_6$-C$_{12}$ aromatic hydrocarbon group (a C$_6$-C$_{12}$ aryl group)" is bonded to —C=O—, i.e., a "C$_6$-C$_{12}$ aromatic hydrocarbon (a C$_6$-C$_{12}$ aryl)-carbonyl group", and examples thereof include benzoyl, 1-naphthoyl, 2-naphthoyl and the like.

In the present specification, the "protected amino group" means an amino group protected by a "protecting group". Examples of the "protecting group" include a C$_{1-6}$ alkyl group, a C$_{2-6}$ alkenyl group, a C$_{6-10}$ aryl group, a C$_{7-14}$ aralkyl group, a C$_{1-6}$ alkyl-carbonyl group, a C$_{1-6}$ alkoxy-carbonyl group, a C$_{2-6}$ alkenyl-oxycarbonyl group, a C$_{6-10}$ aryl-carbonyl group, a C$_{7-14}$ aralkyl-carbonyl group, a C$_{6-10}$ aryl-oxycarbonyl group, a C$_{7-14}$ aralkyl-oxycarbonyl group, a C$_{6-10}$ arylsulfonyl group, a benzhydryl group, a trityl group, a tri-C$_{1-6}$ alkylsilyl group, a 9-fluorenylmethyloxycarbonyl group, a phthaloyl group and the like. The above-mentioned protecting group is optionally substituted by a halogen atom, a C$_{1-6}$ alkyl group, a C$_{1-6}$ alkoxy group or a nitro group.

Specific examples of the protecting group include acetyl, trifluoroacetyl, pivaloyl, tert-butoxycarbonyl, 2,2,2-trichloroethoxycarbonyl, benzyloxycarbonyl, 9-fluorenylmethyloxycarbonyl, benzhydryl, trityl, phthaloyl, allyloxycarbonyl, p-toluenesulfonyl, o-nitrobenzenesulfonyl and the like.

In the present specification, the "C$_{1-6}$ alkyl-carbonyl group" means a group wherein a "C$_{1-6}$ alkyl group" is bonded to —C=O—.

In the present specification, the "C$_{1-6}$ alkoxy-carbonyl group" means a group wherein a "C$_{1-6}$ alkoxy group" is bonded to —C=O—.

In the present specification, the "C$_{2-6}$ alkenyl-oxycarbonyl group" means a group wherein a "C$_{2-6}$ alkenyl group" is bonded to the oxygen atom of —C(=O)O—.

In the present specification, the "$C_{6-10}$ aryl-carbonyl group" means a group wherein a "$C_{6-10}$ aryl group" is bonded to —C=O—.

In the present specification, the "$C_{7-14}$ aralkyl-carbonyl group" means a group wherein a "$C_{7-14}$ aralkyl group" is bonded to —C=O—.

In the present specification, the "$C_{6-10}$ aryl-oxycarbonyl group" means a group wherein a "$C_{6-10}$ aryl group" is bonded to the oxygen atom of —C(=O)O—.

In the present specification, the "$C_{7-14}$ aralkyl-oxycarbonyl group" means a group wherein a "$C_{7-14}$ aralkyl group" is bonded to the oxygen atom of —C(=O)O—.

In the present specification, the "$C_{6-10}$ arylsulfonyl group" means a group wherein a "$C_{6-10}$ aryl group" is bonded to —S(=O)$_2$—.

In the present specification, the "tri-$C_{1-6}$ alkylsilyl group" means —SiH$_3$ tri-substituted by "$C_1$-$C_6$ alkyl groups".

Each group of the formulas (1)-(4) is explained below.

$R^1$ is a $C_1$-$C_{20}$ hydrocarbon group optionally having substituent(s) selected from Group G1 or a hydrogen atom. The number of the substituents for the $C_1$-$C_{20}$ hydrocarbon group is preferably 1 to 3. When it is 2 or more, these substituents may be the same or different.

$R^1$ is
preferably a $C_1$-$C_{20}$ hydrocarbon group optionally having substituent(s) selected from Group G1,
more preferably a $C_1$-$C_{20}$ alkyl group optionally having substituent(s) selected from Group G1, a $C_3$-$C_{20}$ cycloalkyl group optionally having substituent(s) selected from Group G1 or a $C_6$-$C_{20}$ aryl group optionally having substituent(s) selected from Group G1,
further more preferably a $C_1$-$C_{12}$ alkyl group optionally having substituent(s) selected from Group G1, a $C_3$-$C_{12}$ cycloalkyl group optionally having substituent(s) selected from Group G1 or a $C_6$-$C_{12}$ aryl group optionally having substituent(s) selected from Group G1,
still more preferably a $C_1$-$C_8$ alkyl group optionally having substituent(s) selected from Group G1, a $C_3$-$C_8$ cycloalkyl group optionally having substituent(s) selected from Group G1 or a $C_6$-$C_{10}$ aryl group optionally having substituent(s) selected from Group G1,
particularly preferably a $C_1$-$C_6$ alkyl group optionally having substituent(s) selected from Group G1 (preferably a $C_6$-$C_{10}$ aryl group, a $C_1$-$C_{12}$ alkoxy group having $C_6$-$C_{10}$ aryl group(s)), a $C_3$-$C_8$ cycloalkyl group, a $C_6$-$C_{10}$ aryl group (preferably a phenyl group) optionally having substituent(s) selected from Group G1 (preferably a halogen atom, a $C_1$-$C_6$ alkoxy group, a $C_1$-$C_6$ fluorinated alkyl group).

$Ar^1$ and $Ar^2$ are each independently a phenyl group optionally having substituent(s) selected from Group G2, a $C_1$-$C_{12}$ chain hydrocarbon group, a $C_3$-$C_{12}$ alicyclic hydrocarbon group or a hydrogen atom. The number of the substituents for the phenyl group is preferably 1 to 3. When it is 2 or more, these substituents may be the same or different.

$Ar^1$ and $Ar^2$ are
preferably each independently a phenyl group optionally having substituent(s) selected from Group G2,
more preferably each independently a phenyl group optionally having $C_1$-$C_{12}$ fluorinated alkyl group(s),
further more preferably each independently a phenyl group optionally having $C_1$-$C_4$ fluorinated alkyl group(s),
still more preferably each independently a phenyl group optionally having trifluoromethyl group(s),
still more preferably both phenyl groups or both 3,5-bis(trifluoromethyl)phenyl groups,
particularly preferably both 3,5-bis(trifluoromethyl)phenyl groups.

$R^5$ is a hydrogen atom, a fluorine atom, a hydroxyl group, a $C_1$-$C_{12}$ alkoxy group, a $C_1$-$C_{12}$ fluorinated alkyloxy group or a silyloxy group represented by —OSiR$^6$R$^7$R$^8$ wherein R$^6$, R$^7$ and R$^8$ are each independently a $C_1$-$C_8$ alkyl group or a $C_6$-$C_{20}$ aryl group.

$R^5$ is
preferably a hydroxyl group or a silyloxy group represented by —OSiR$^6$R$^7$R$^8$ wherein R$^6$, R$^7$ and R$^8$ are as defined above,
more preferably a hydroxyl group or a silyloxy group represented by —OSiR$^6$R$^7$R$^8$ wherein R$^6$, R$^7$ and R$^8$ are each independently a $C_1$-$C_8$ alkyl group (preferably a methyl group), further more preferably a silyloxy group represented by —OSiR$^6$R$^7$R$^8$ wherein R$^6$, R$^7$ and R$^8$ are each independently a $C_1$-$C_8$ alkyl group (preferably a methyl group),
still more preferably a silyloxy group represented by —OSiR$^6$R$^7$R$^8$ wherein R$^6$, R$^7$ and R$^8$ are each independently a $C_1$-$C_4$ alkyl group (preferably a methyl group),
particularly preferably a trimethylsilyloxy group.

Preferable combination of $Ar^1$, $Ar^2$ and $R^5$ is as follows:
(1) An embodiment wherein $Ar^1$ and $Ar^2$ are each independently a phenyl group optionally having substituent(s) selected from Group G2, and $R^5$ is a silyloxy group represented by —OSiR$^6$R$^7$R$^8$ wherein R$^6$, R$^7$ and R$^8$ are as defined above.
(2) An embodiment wherein $Ar^1$ and $Ar^2$ are each independently a phenyl group optionally having $C_1$-$C_{12}$ fluorinated alkyl group(s), and $R^5$ is a silyloxy group represented by —OSiR$^6$R$^7$R$^8$ wherein R$^6$, R$^7$ and R$^8$ are each independently a $C_1$-$C_8$ alkyl group (preferably a methyl group).
(3) An embodiment wherein $Ar^1$ and $Ar^2$ are each independently a phenyl group optionally having $C_1$-$C_4$ fluorinated alkyl group(s), and $R^5$ is a silyloxy group represented by —OSiR$^6$R$^7$R$^8$ wherein R$^6$, R$^7$ and R$^8$ are each independently a $C_1$-$C_4$ alkyl group (preferably a methyl group).
(4) An embodiment wherein $Ar^1$ and $Ar^2$ are each independently a phenyl group optionally having trifluoromethyl group(s), and $R^5$ is a trimethylsilyloxy group.
(5) An embodiment wherein $Ar^1$ and $Ar^2$ are both phenyl groups or both 3,5-bis(trifluoromethyl)phenyl groups, and $R^5$ is a trimethylsilyloxy group.
(6) An embodiment wherein $Ar^1$ and $Ar^2$ are both 3,5-bis(trifluoromethyl)phenyl groups, and $R^5$ is a trimethylsilyloxy group.

$R^2$ is a $C_1$-$C_{20}$ hydrocarbon group optionally having substituent(s) selected from Group G1, a $C_1$-$C_{12}$ alkoxy group optionally having substituent(s) selected from Group G1, a $C_1$-$C_{12}$ alkylthio group optionally having substituent(s) selected from Group G1, a protected amino group, a heterocyclic group optionally having substituent(s) selected from Group G2 or a hydrogen atom.

$R^2$ is
preferably a $C_1$-$C_{20}$ hydrocarbon group optionally having substituent(s) selected from Group G1 or a $C_1$-$C_{12}$ alkoxy group optionally having substituent(s) selected from Group G1,
more preferably a $C_1$-$C_{12}$ alkyl group optionally having substituent(s) selected from Group G1 or a $C_1$-$C_{12}$ alkoxy group optionally having substituent(s) selected from Group G1,
further more preferably a $C_1$-$C_8$ alkyl group optionally having substituent(s) selected from Group G1 or a $C_1$-$C_8$ alkoxy group optionally having substituent(s) selected from Group G1,
still more preferably a $C_1$-$C_4$ alkyl group optionally having substituent(s) selected from Group G1 or a $C_1$-$C_4$ alkoxy group optionally having substituent(s) selected from Group G1, particularly preferably a $C_1$-$C_4$ alkyl group or a $C_1$-$C_4$ alkoxy group optionally having $C_6$-$C_{10}$ aryl group(s).

$R^X$ is an amino-protecting group.

$R^X$ is preferably a $C_{6-10}$ arylsulfonyl group optionally having substituent(s) (preferably a $C_{1-6}$ alkyl group or a nitro group), more preferably a benzenesulfonyl group optionally having $C_{1-6}$ alkyl group(s) or nitro group(s), further more preferably a p-toluenesulfonyl group (a tosyl (Ts) group), an o-nitrobenzenesulfonyl group (an o-nosyl (o-Ns) group) or a p-nitrobenzenesulfonyl group (a p-nosyl (p-Ns) group), particularly preferably a p-toluenesulfonyl group (a tosyl (Ts) group) or a p-nitrobenzenesulfonyl group (a p-nosyl (p-Ns) group).

$Ar^X$ is a phenyl group optionally having substituent(s) selected from Group G2.

$Ar^X$ is preferably a phenyl group.

In the present invention, optically active β-aminoaldehyde (3) is produced by a step of reacting imine compound (1-1) or a precursor thereof, i.e., sulfone compound (1-2) with aldehyde compound (2) in the presence of optically active pyrrolidine compound (4) as a catalyst (Mannich reaction step).

Sulfone compound (1-2) can be produced according to the method described in Synthesis 2000, 75. For example, when $R^X$ is a substituted $C_{6-10}$ arylsulfonyl group (e.g. a tosyl group, an o-nosyl group or a p-nosyl group etc.), it can be produced by reacting the corresponding aldehyde ($R^1$CHO) with the corresponding $C_{6-10}$ arenesulfonamide and the corresponding sodium sulphinate ($Ar^XSO_2Na$) in the presence of formic acid. Imine compound (1-1) can be produced by eliminating —$SO_2Ar^X$ from sulfone compound (1-2).

The use of Sulfone compound (1-2) is convenient since the Mannich reaction progresses together with elimination of $SO_2Ar^X$.

The amount of aldehyde compound (2) to be used is preferably 1-10 mol, more preferably 3-7 mol, relative to imine compound (1-1) or sulfone compound (1-2), in view of yield, selectivity and economic efficiency.

The catalyst, optically active pyrrolidine compound (4) is preferably a pyrrolidine compound represented by the formula (4a):

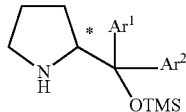

(4a)

wherein
$Ar^1$, $Ar^2$ and * are as defined above,
TMS is a trimethylsilyl group, and
the carbon atom marked with * is an asymmetric carbon atom, in view of diastereoselectivity (when $R^2$ in aldehyde compound (2) is not a hydrogen atom), though depending on the kind of imine compound (1-1) or sulfone compound (1-2) and aldehyde compound (2). Among them, a pyrrolidine compound wherein $Ar^1$ and $Ar^2$ are each independently a phenyl group optionally having $C_1$-$C_4$ fluorinated alkyl group(s) is preferable,
a pyrrolidine compound wherein $Ar^1$ and $Ar^2$ are each independently a phenyl group optionally having trifluoromethyl group(s) is more preferable,
a pyrrolidine compound wherein $Ar^1$ and $Ar^2$ are both phenyl groups or both 3,5-bis(trifluoromethyl)phenyl groups is still more preferable, and
a pyrrolidine compound wherein $Ar^1$ and $Ar^2$ are both 3,5-bis(trifluoromethyl)phenyl groups is particularly preferable.

The amount of optically active pyrrolidine compound (4) to be used is preferably 0.5-30 mol %, more preferably 1-20 mol %, particularly preferably 5-15 mol %, relative to imine compound (1-1) or sulfone compound (1-2), in view of yield and economic efficiency.

The Mannich reaction of the present invention is preferably carried out in the presence of a base. Examples of the base include sodium hydrogen carbonate, potassium hydrogen carbonate and the like. Among them, sodium hydrogen carbonate is preferable in view of economic efficiency.

The amount of the base to be used is preferably 1-10 mol, more preferably 1-5 mol, relative to imine compound (1-1) or sulfone compound (1-2), in view of yield and economic efficiency.

The Mannich reaction of the present invention is preferably carried out in a solvent. Examples of the solvent to be used in the present invention include aromatic hydrocarbon solvents (e.g., toluene, benzene, xylene); alcohol solvents (e.g., methanol, ethanol); halogenated hydrocarbon solvents (e.g., chloroform, dichloromethane, carbon tetrachloride); ether solvents (e.g., diethyl ether, tetrahydrofuran, 1,4-dioxane); nitrile solvents (e.g., acetonitrile); aprotic polar solvents (e.g., dimethylformamide, dimethylacetamide); water; mixed solvents thereof, and the like.

Among them, though depending on the kind of imine compound (1-1) or sulfone compound (1-2) and aldehyde compound (2), in view of enantioselectivity and diastereoselectivity (when $R^2$ in aldehyde compound (2) is not a hydrogen atom), ether solvents (preferably tetrahydrofuran, 1,4-dioxane, more preferably 1,4-dioxane), halogenated hydrocarbon solvents (preferably dichloromethane), water, and mixed solvents of water and a halogenated hydrocarbon solvent (preferably dichloromethane) are preferable, and in view of good yield, superior enantioselectivity and diastereoselectivity (when $R^2$ in aldehyde compound (2) is not a hydrogen atom), ether solvents (preferably tetrahydrofuran, 1,4-dioxane, more preferably 1,4-dioxane), water, and mixed solvents of water and a halogenated hydrocarbon solvent (preferably dichloromethane) are more preferable, and ether solvents (preferably tetrahydrofuran, 1,4-dioxane, more preferably 1,4-dioxane) and water are still more preferable, and 1,4-dioxane and water are particularly preferable.

When water is used, water containing an inorganic salt is preferably used in view of yield. Examples of the inorganic salt include sodium chloride, potassium chloride, sodium sulfate and the like. Among them, sodium chloride is preferable in view of economic efficiency. The water containing an inorganic salt is preferably used within the range from a 5 wt % aqueous solution to a saturated aqueous solution. When sodium chloride is used, a saturated aqueous solution thereof is particularly preferably used.

When the solvent is a mixed solvent of water and a halogenated hydrocarbon solvent, the amount of water to be used is preferably 0.3-5 mL, more preferably 0.5-2 mL, per 1 mL of the halogenated hydrocarbon solvent.

The amount of the solvent to be used is preferably 0.2-50 mL, more preferably 1-10 mL, per 1 mmol of imine compound (1-1) or sulfone compound (1-2).

The Mannich reaction of the present invention is carried out by a method of adding aldehyde compound (2) to a mixture of imine compound (1-1) or sulfone compound (1-2), optically active pyrrolidine compound (4), a base and a solvent; or the like.

The Mannich reaction of the present invention is preferably carried out within the range of 0-100° C., more preferably within the range of 0-40° C., though depending on the kind of imine compound (1-1) or sulfone compound (1-2) and aldehyde compound (2).

While the reaction time varies depending on the kind of imine compound (1-1) or sulfone compound (1-2) and aldehyde compound (2), and the reaction temperature, it is preferably 1-100 hr, more preferably 10-50 hr.

The progress of the reaction can be confirmed by an analysis means such as thin layer chromatography, gas chromatography, high performance liquid chromatography and the like.

Optically active β-aminoaldehyde compound (3) contained in thus obtained reaction mixture can be isolated by subjecting the reaction mixture to a post-treatment using a conventional method (e.g., neutralization, extraction, washing with water, distillation, crystallization etc.), and purified by subjecting optically active β-aminoaldehyde compound (3) to recrystallization treatment, extraction purification treatment, distillation treatment, adsorption treatment using activated carbon, silica, alumina and the like, or chromatography treatment using silica gel column chromatography and the like.

Optically active β-aminoaldehyde compound (3) is not always stable, and, in some cases, it may be isomerized during isolation and/or purification from the reaction mixture. Therefore, the diastereo ratio (syn/anti ratio) and enantiomeric excess (ee(%)) of optically active β-aminoaldehyde compound (3) are desirably determined without isolation and/or purification after completion of the aldol reaction, but after conversion of optically active β-aminoaldehyde compound (3) to a compound free of isomerization during reaction, isolation and purification. In the present invention, optically active β-aminoaldehyde compound (3) is converted to a corresponding optically active amidoalcohol compound (an optically active amidoalcohol compound represented by the formula (5):

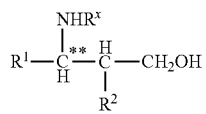

(5)

wherein $R^1$, $R^2$ and $R^X$ are as defined above.

Optically active amidoalcohol compound (5) is produced by a step of reducing the reaction mixture after completion of the Mannich reaction which contains optically active β-aminoaldehyde compound (3), or optically active β-aminoaldehyde compound (3) without purification.

The reduction reaction is carried out using a reducing agent in a solvent.

Examples of the reducing agent include sodium borohydride, sodium cyanoborohydride, lithium aluminum hydride, sodium aluminum hydride and the like. Among them, sodium borohydride is preferable in view of yield and economic efficiency.

The amount of the reducing agent to be used is preferably 1-100 mol, preferably 5-15 mol, per 1 mol of optically active β-aminoaldehyde compound (3), in view of yield and economic efficiency.

Examples of the solvent to be used for the reduction reaction include alcohol solvents (e.g., methanol, ethanol, 2-propanol); water; mixed solvents thereof, and the like. Among them, alcohol solvents (e.g., methanol, ethanol) are preferable in view of yield and reactivity.

The amount of the solvent to be used is preferably 1-100 mL, more preferably 5-20 mL, per 1 g of optically active β-aminoaldehyde compound (3).

The reduction reaction is carried out by a method of adding a reducing agent to a solution prepared by dissolving optically active β-aminoaldehyde compound (3) in a solvent; a method of adding optically active β-aminoaldehyde compound (3) to a dispersion prepared by a reducing agent in a solvent; or the like. In view of yield and operability, the reaction is preferably carried out by a method of adding a reducing agent to a solution prepared by dissolving optically active β-aminoaldehyde compound (3) in a solvent.

The reduction reaction is preferably carried out within the range of −20-100° C., more preferably within the range of −10-30° C., though depending on the kind of optically active β-aminoaldehyde compound (3) and the reducing agent.

While the reaction time varies depending on the kind of optically active β-aminoaldehyde compound (3) and the reducing agent, and the reaction temperature, it is preferably 10 min-10 hr, more preferably 30 min-2 hr.

The progress of the reaction can be confirmed by an analysis means such as thin layer chromatography, gas chromatography, high performance liquid chromatography and the like.

Optically active amidoalcohol compound (5) contained in thus obtained reaction mixture can be isolated by subjecting the reaction mixture to a post-treatment using a conventional method (e.g., neutralization, extraction, washing with water, distillation, crystallization etc.), and purified by subjecting optically active amidoalcohol compound (5) to recrystallization treatment, extraction purification treatment, distillation treatment, adsorption treatment using activated carbon, silica, alumina and the like, or chromatography treatment using silica gel column chromatography and the like.

The diastereo ratio (syn/anti ratio) and enantiomeric excess of the obtained optically active amidoalcohol compound (5) are determined. The measured diastereo ratio (syn/anti ratio) and enantiomeric excess correspond to those of optically active β-aminoaldehyde compound (3).

When $R^2$ in aldehyde compound (2) is not a hydrogen atom, in the Mannich reaction step of the present invention, the anti-form of optically active β-aminoaldehyde compound (3) is preferentially obtained. The diastereoselectivity showing a diastereo ratio (syn/anti ratio) of, for example, 50/50 or more, or, for example, 20/80 or more, is available.

In the Mannich reaction step of the present invention, when pyrrolidine compound (4a) wherein the absolute configuration of C* is S-configuration, i.e., a pyrrolidine compound represented by the formula (4a-S):

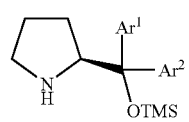

(4a-S)

wherein $Ar^1$ and $Ar^2$ are as defined above, and TMS is a trimethylsilyl group,
is used as a catalyst, optically active β-aminoaldehyde compound (3) wherein the absolute configuration of C* is S-configuration, i.e., an optically active β-aminoaldehyde compound represented by the formula (3R):

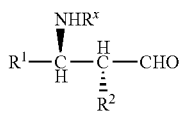

wherein $R^1$, $R^2$ and Rx are as defined above,
is preferentially obtained.

On the other hand, pyrrolidine compound (4a) wherein the absolute configuration of C* is R-configuration, i.e., a pyrrolidine compound represented by the formula (4a-R):

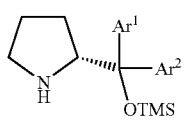

wherein $Ar^1$ and $Ar^2$ are as defined above, and TMS is a trimethylsilyl group,
is used as a catalyst, optically active β-aminoaldehyde compound (3) wherein the absolute configuration of C* is R-configuration, i.e., an optically active β-aminoaldehyde compound represented by the formula (3S):

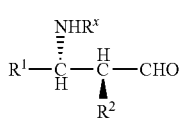

wherein $R^1$, $R^2$ and Rx are as defined above,
is preferentially obtained.

Therefore, in the Mannich reaction step of the present invention, the enantioselectivity showing an enantiomeric excess of, for example, 50ee % or more, or, for example, 80ee % or more, is available.

Example

The present invention is explained in detail in the following by referring to Examples.

All reactions were carried out under argon atmosphere and monitored by thin-layer chromatography using Merck 60 F254 precoated silica gel plates (0.25 mm thickness).

FT-IR spectra were recorded on a JASCO FT/IR-410 spectrometer.

$^1$H and $^{13}$C NMR spectra were recorded on a Bruker AM400 (400 MHz for $^1$H NMR, 100 MHz for $^{13}$C NMR) instrument. Data for $^1$H NMR are reported as chemical shift (δ ppm), multiplicity (s=singlet, d=doublet, t=triplet, q=quartet, m=multiplet), coupling constant (Hz), integration and assignment. Data for $^{13}$C NMR are reported as chemical shift. High-resolution mass spectral analyses (HRMS) were carried out using Bruker ESI-TOF MS.

All liquid aldehydes and solvents were distilled before use.

Preparative thin layer chromatography was performed using Wakogel B-5F purchased from Wako Pure Chemical Industries (Tokyo, Japan). Flash chromatography was performed using silica gel 60N of Kanto Chemical Co. Int. (Tokyo, Japan).

HPLC analysis was performed on a HITACHI Elite LaChrom Series HPLC, while UV detection was monitered at appropriate wavelength respectively, using CHIRALCEL OJ-H (0.46 cm×25 cm), CHIRALPAK AD-H (0.46 cm×25 cm), CHIRALPAK AS-H (0.46 cm×25 cm), CHIRALPAK IA (0.46 cm×25 cm), CHIRALPAK IB (0.46 cm×25 cm) and CHIRALPAK IC (0.46 cm×25 cm).

Reference Examples 1-1-1-7

Production of Sulfone Compound

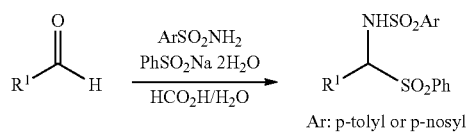

A mixture of aldehyde (5 mmol), arenesulfonamide (5 mmol), and sodium benzenesulfinate dihydrate (5.5 mmol) in formic acid (7.5 mL) and $H_2O$ (7.5 mmol) was stirred at 23° C. for 12 h. The resulting white precipitate was collected by filtration, washed successively with $H_2O$ (10 mL) and hexane (10 mL), and dissolved in $CH_2Cl_2$ (30 mL), and the solution was dried over $Na_2SO_4$, and filtration. The solvent was evaporated, and to the residue was added hexane. The resulting precipitate was collected by filtration, and dried under reduced pressure to give the corresponding sulfone compound.

N-(3-phenyl-1-(phenylsulfonyl)propyl)-p-toluenesulfonamide

Reference Example 1-1

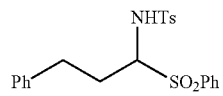

$^1$H NMR (CDCl$_3$, 400 MHz): δ 1.90-2.01 (1H, m), 2.40 (3H, s), 2.43-2.71 (3H, m), 4.61 (1H, ddd, J=4.0, 9.6, 8.8 Hz), 5.49 (1H, br-s), 7.04 (2H, d, J=6.8 Hz), 7.17-7.28 (5H, m), 7.46-7.55 (4H, m), 7.65 (1H, t, J=7.6 Hz), 7.82 (2H, d, J=7.6 Hz);
$^{13}$C NMR (CDCl$_3$, 100 MHz): δ 21.5, 30.3, 31.2, 73.1, 126.4, 126.8, 128.3, 128.6, 129.1, 129.6, 129.7, 134.2, 135.8, 137.6, 139.6, 143.9;
IR (KBr): ν 3321, 2955, 2928, 1448, 1341, 1299, 1160, 1145, 1081, 959, 813, 751 cm$^{-1}$;
HRMS (ESI): [M+Na] calculated for ([C$_{22}$H$_{23}$O$_4$S$_2$NNa]): 452.0961. found 452.0969.

N-(3-methyl-1-(phenylsulfonyl)butyl)-p-toluenesulfonamide

Reference Example 1-2

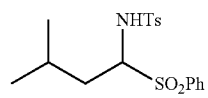

$^1$H NMR (CDCl$_3$, 400 MHz): δ 0.77 (3H, dd, J=2.0, 6.4 Hz), 0.85 (3H, dd, J=1.2, 6.4 Hz), 1.43-1.53 (1H, m), 1.59 (1H, ddd, J=4.0, 10.8, 14.4 Hz), 1.93 (1H, ddd, J=3.2, 10.0, 13.6 Hz), 2.39 (3H, s), 4.66 (1H, dt, J=3.2, 10.4 Hz), 5.61-

5.77 (br-m), 7.20 (2H, d, J=8.4 Hz), 7.52 (2H, t, J=8.0 Hz), 7.56 (2H, d, J=8.0 Hz), 7.65 (1H, t, J=7.6 Hz), 7.84 (2H, d, J=7.2 Hz);

$^{13}$C NMR (CDCl$_3$, 100 MHz): δ 21.0, 21.5, 13.2, 24.0, 37.0, 72.7, 126.7, 129.1, 129.5, 129.7, 134.2, 135.6, 137.8, 143.7;

IR (KBr): ν 3239, 2952, 2871, 1596, 1459, 1330, 1286, 1071, 906, 812, 676 cm$^{-1}$; HRMS (ESI): [M+Na] calculated for ([C$_{18}$H$_{23}$O$_4$S$_2$NNa]): 404.0961. found 404.0946.

N-(2-methyl-1-(phenylsulfonyl)propyl)-p-toluenesulfonamide

Reference Example 1-3

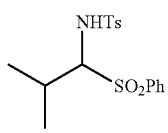

$^1$H NMR (CDCl$_3$, 400 MHz): δ 0.85 (3H, d, J=6.8 Hz), 1.04 (3H, d, J=6.8 Hz), 2.39 (3H, s), 2.60-2.77 (1H, m), 4.53 (1H, dd, J=2.8, 10.8 Hz), 5.49 (1H, br-d, J=10.8), 7.17 (2H, d, J=8.4 Hz), 7.48 (2H, br-b, J=8.0 Hz), 7.63 (1H, br-t, J=7.2 Hz), 7.84 (2H, br-d, J=7.2 Hz);

$^{13}$C NMR (CDCl$_3$, 100 MHz): δ 16.6, 20.9, 21.5, 27.6, 77.6, 126.6, 129.1, 129.3, 129.6, 134.0, 137.1, 138.0, 143.6;

IR (KBr): ν 3300, 2967, 2932, 1470, 1419, 1342, 1307, 1166, 1135, 1083, 1055, 887, 669 cm$^{-1}$;

HRMS (ESI): [M+Na] calculated for ([C$_{17}$H$_{21}$O$_4$S$_2$NNa]): 390.0804. found 390.0798.

N-(cyclohexyl(phenylsulfonyl)methyl)-p-toluenesulfonamide

Reference Example 1-4

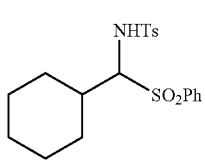

$^1$H NMR (CDCl$_3$, 400 MHz): δ 0.90-1.09 (3H, m), 1.28 (2H, tq, J=2.8, 12.8 Hz), 1.53-1.79 (3H, m), 2.01 (1H, br-d, J=12.4 Hz), 2.40 (4H, s), 4.48 (1H, dd, J=3.2, 10.8 Hz), 5.25 (1H, d, J=10.8 Hz), 7.17 (2H, d, J=8.4 Hz), 7.42-7.49 (4H, m), 7.62 (1H, t, J=7.6 Hz), 7.80 (2H, br-d, J=7.6 Hz);

$^{13}$C NMR (CDCl$_3$, 100 MHz): δ 21.4, 25.4, 25.5, 26.0, 27.1, 30.8, 37.2, 77.7, 124.9, 126.3, 126.5, 128.9, 129.0, 129.2, 129.4, 129.5, 133.8, 136.9, 137.9, 143.4; IR (KBr): ν 3301, 2934, 2854, 1446, 1337, 1304, 1162, 1146, 1079, 751, 676 cm$^{-1}$;

HRMS (ESI): [M+Na] calculated for ([C$_{20}$H$_{25}$O$_4$S$_2$NNa]): 430.1117. found 430.1125.

N-(2-phenyl-1-(phenylsulfonyl)ethyl)-p-toluenesulfonamide

Reference Example 1-5

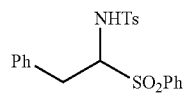

$^1$H NMR (CDCl$_3$, 400 MHz): δ 2.32 (3H, s), 2.30 (1H, dd, J=10.4, 14.4 Hz), 3.60 (1H, dd, J=3.6, 14.4 Hz), 4.85 (1 h, dt, J=3.6, 10.0 Hz), 6.06 (1H, br-s), 6.92 (2H, d, J=8.0 Hz), 6.99-7.10 (5H, m), 7.14 (2H, d, J=8.0 Hz), 7.59 (2H, t, J=7.2 Hz), 7.70 (1H, t, J=7.2 Hz), 8.02 (2H, br-d, J=7.6 Hz);

$^{13}$C NMR (CDCl$_3$, 100 MHz): δ 21.4, 33.6, 75.4, 126.1, 126.9, 128.6, 129.1, 129.5, 129.6, 130.1, 134.1, 134.4, 135.5, 137.4, 143.0;

IR (KBr): ν 3251, 3031, 2921, 1597, 14977, 1449, 1427, 1337, 1314, 1161, 1076, 732, 666 cm$^{-1}$;

HRMS (ESI): [M+Na] calculated for ([C$_{21}$H$_{21}$O$_4$S$_2$NNa]): 438.0804. found 438.0784.

N-(2-benzyloxy-1-(phenylsulfonyl)ethyl)-p-toluenesulfonamide

Reference Example 1-6

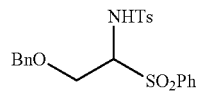

$^1$H NMR (CDCl$_3$, 400 MHz): δ 2.37 (3H, s), 3.65 (1H, dd, J=4.0, 10.8 Hz), 4.05 (1H, dd, J=3.6, 10.8 Hz), 4.36 (1H, d, J=12.0 Hz), 4.41 (1H, d, J=12.0 Hz), 4.67-4.75 (1H, m), 5.96 (1H, br-s), 7.12-7.18 (4H, m), 7.27-7.32 (3H, m), 7.46 (2H, t, J=7.6 Hz), 7.56-7.65 (3H, m), 7.81 (2 h, d, J=7.6 Hz);

$^{13}$C NMR (CDCl$_3$, 100 MHz): δ 21.5, 65.7, 72.8, 73.5, 126.9, 127.8, 127.9, 128.3, 128.9, 129.5, 129.6, 134.1, 136.2, 136.6, 137.3, 143.8;

IR (KBr): ν 3289, 3248, 2863, 1446, 1308, 1164, 1137, 1081, 949, 811, 666, 549 cm$^{-1}$;

HRMS (ESI): [M+Na] calculated for ([C$_{22}$H$_{23}$O$_5$S$_2$NNa]): 468.0910. found 468.0917.

N-(cyclohexyl(phenylsulfonyl)methyl)-p-nitrobenzenesulfonamide

Reference Example 1-7

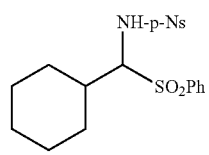

$^1$H NMR (CDCl$_3$, 400 MHz): δ 0.98-1.13 (3H, m), 1.21-1.35 (2H, m), 1.57-1.81 (4H, m), 1.99-2.08 (1H, m), 2.33 (1H, tq, J=12.0, 3.2 Hz), 4.54 (1H, dd, J=2.8, 10.8 Hz), 5.65 (1H, d, J=10.8 Hz), 7.46 (2H, t, J=8.0 Hz), 7.63 (1H, t, J=7.6 Hz), 7.74-7.80 (3H, m), 8.21 (2H, br-d, J=8.8 Hz);

$^{13}$C NMR (CDCl$_3$, 100 MHz): δ 25.5, 26.0, 26.9, 31.1, 37.5, 77.2, 77.7, 124.3, 127.9, 129.1, 129.3, 134.3, 137.0, 146.2, 150.0;

IR (KBr): ν 3276, 2933, 2858, 1537, 1445, 1352, 1306, 1171, 1148, 1079, 851, 740 cm$^{-1}$;

HRMS (ESI): [M+Na] calculated for ([C$_{19}$H$_{22}$O$_6$S$_2$N$_2$Na]): 461.0811. found 461.0823.

Examples 1-1-1-8

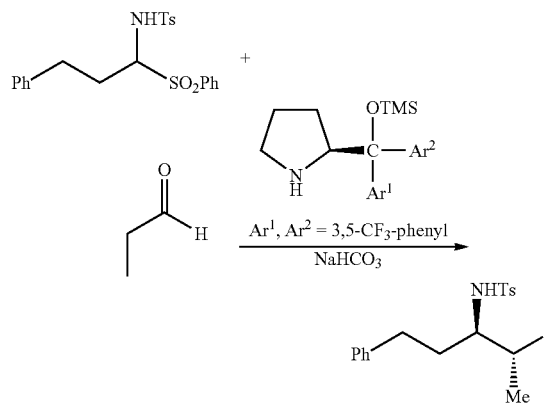

To a mixture of the sulfone compound obtained in Reference Example 1-1 (0.2 mmol), pyrrolidine compound (12.0 mg, 0.02 mmol) as a catalyst and NaHCO$_3$ (50.4 mg, 0.6 mmol) in the solvent shown in Table 1 (0.4 mL) was added propanal (1.0 mmol) at 10° C. The reaction mixture was stirred at the temperature shown in Table 1 for 20 hr (stirred for 48 hr in Example 1-8), and the reaction was quenched by addition of aqueous NaHCO$_3$. The reaction mixture was extracted with chloroform (3×10 mL), and the combined organic layer were dried over Na$_2$SO$_4$, filtered, and concentrated under reduced pressure. The residue was purified by column chromatography (EtOAc:hexane=1:7) to give N-((2R,3R)-2-methyl-1-oxo-5-phenylpentan-3-yl)-p-toluenesulfonamide. The yield is shown in Table 1. The syn/anti ratio was determined by $^1$H-NMR spectrum after conversion to the corresponding amidoalcohol by reduction with NaBH$_4$ (according to the method shown in Reference Example 2). The enantiomeric excess was determined by HPLC equipped with CHIRALPAK IB column ($^i$PrOH:hexane=1:10) (1.0 mL/min, the retention time of the minor enantiomer=14.9 min, the retention time of the major enantiomer=13.3 min), after conversion to the corresponding amidoalcohol by reduction with NaBH$_4$ (according to the method shown in Reference Example 2). The syn/anti ratio and enantiomeric excess are shown in Table 1.

TABLE 1

| Example | Solvent | Temperature (° C.) | Yield (%) | anti:syn | ee (%) |
|---|---|---|---|---|---|
| 1-1 | CH$_2$Cl$_2$ | 0 | 38 | 76:24 | 97 |
| 1-2 | THF | 0 | 52 | 95:5 | 98 |
| 1-3 | 1,4-dioxane | 0 | 62 | 92:8 | 98 |
| 1-4 | H$_2$O | 0 | 41 | 93:7 | 96 |
| 1-5 | saturated brine | 0 | 60 | 89:11 | 96 |
| 1-6 | saturated brine/CH$_2$Cl$_2$ (1/1) (volume ratio) | 0 | 49 | >95:5 | 97 |
| 1-7 | saturated brine | 10 | 76 | 84:16 | 94 |
| 1-8 | 1,4-dioxane | 10 | 79 | 88:12 | 96 |

Example 2-1-2-14

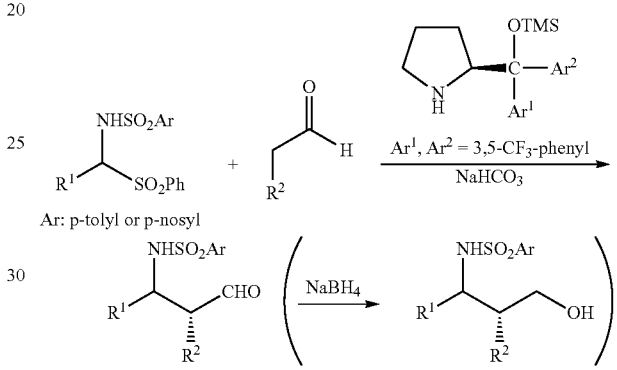

To a mixture of the sulfone compound obtained in Reference Examples 1-1-1-7 or the corresponding imine compound (0.2 mmol, used in Examples 2-10-2-14), pyrrolidine compound (12.0 mg, 0.02 mmol) as a catalyst and NaHCO$_3$ (50.4 mg, 0.6 mmol, not used in Example 2-10) in saturated brine (0.4 mL) or 1,4-dioxane (0.4 mL) was added the corresponding aldehyde (1.0 mmol) at 10° C. The reaction mixture was stirred (stirred for 20 hr when brine was used as a solvent, and stirred for 48 hr when 1,4-dioxane was used as a solvent), and the reaction was quenched by the addition of aqueous NaHCO$_3$. The reaction mixture was extracted with chloroform (3×10 mL), and the combined organic layer was dried over Na$_2$SO$_4$, filtered, and concentrated under reduced pressure. The residue was purified by column chromatography (EtOAc:hexane=1:7) to give the corresponding β-aminoaldehyde compound. The yield is shown in Table 2. The syn/anti ratio was determined by $^1$H-NMR spectrum after conversion to the corresponding amidoalcohol by reduction with NaBH$_4$ (according to the method shown in Reference Example 2). The enantiomeric excess was determined by chiral HPLC after conversion to the corresponding amidoalcohol by reduction with NaBH$_4$ (according to the method shown in Reference Example 2). The syn/anti ratio and enantiomeric excess are shown in Table 2. In Examples 2-8, 2-9, 2-11-2-14, the mixture after completion of the Mannich reaction was reduced with NaBH$_4$ (according to the method shown in Reference Example 2) to convert to the corresponding amidoalcohol, and the amidoalcohol was isolated.

N-((2R,3R)-2-methyl-1-oxo-5-phenylpentan-3-yl)-p-toluenesulfonamide

Example 2-1

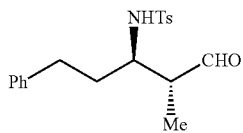

$^1$H NMR (CDCl$_3$, 400 MHz): δ 1.10 (3, d, J=7.2 Hz), 1.57-1.77 (2H, m), 2.32-2.52 (5H, m), 2.68 (1H, dq, J=4.0, 7.2 Hz), 3.55-3.64 (1H, m), 5.09 (1H, d, J=8.8 Hz), 6.96 (2H, d, J=7.2 Hz), 7.13-7.25 (3H, m), 7.30 (2H, d, J=8.4 Hz), 9.53 (1H, s);

$^{13}$C NMR (CDCl$_3$, 100 MHz): δ 9.81, 21.5, 32.1, 34.3, 49.9, 54.2, 126.1, 127.0, 128.2, 128.4, 129.8, 138.1, 140.6, 143.6, 203.1;

IR (neat): ν 3279, 3028, 2929, 1721, 1454, 1326, 1160, 1092, 702, 666 cm$^{-1}$;

HRMS (ESI): [M+Na] calculated for ([C$_{19}$H$_{23}$NNaO$_3$S]): 368.1291. found 368.1308;

[α]$_D^{20°}$ C. +17.1 (c 0.35, CHCl$_3$);

The enantiomeric excess of the corresponding amidoalcohol after reduction was determined by HPLC equipped with CHIRALPAK IB column ($^i$PrOH:hexane=1:10) (1.0 mL/min, the retention time of the minor enantiomer=14.9 min, the retention time of the major enantiomer=13.3 min).

N-((2R,3R)-2,5-dimethyl-1-oxohexan-3-yl)-p-toluenesulfonamide

Example 2-2

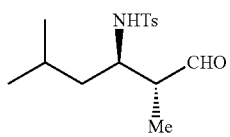

$^1$H NMR (CDCl$_3$, 400 MHz): δ 0.64 (3H, d, J=6.8 Hz), 0.76 (3H, d, J=6.8 Hz), 1.10 (3H, d, J=Hz), 1.15-1.27 (1H, m), 1.30-1.42 (2H, m), 2.42 (3H, s), 2.69 (1H, dq, J=3.2, 7.2 Hz), 3.60-3.68 (1H, m), 4.82 (1H, d, J=8.4 Hz), 7.30 (2H, d, J=8.4 Hz), 7.76 (2H, d, J=8.4 Hz), 9.57 (1H, s);

$^{13}$C NMR (CDCl$_3$, 100 MHz): δ 9.33, 21.5, 21.6, 22.9, 24.5, 41.7, 50.1, 52.3, 127.1, 129.7, 138.0, 143.5, 203.2;

IR (neat): ν 3279, 2958, 2871, 1719, 1463, 1427, 1330, 1281, 1160, 1093, 816, 667, 552 cm$^{-1}$;

HRMS (ESI): [M+Na] calculated for ([C$_{15}$H$_{23}$NNaO$_3$S]): 320.1291. found 320.1293;

[α]$_D^{20°}$ C. +19.5 (c 1.61, CHCl$_3$);

The enantiomeric excess of the corresponding amidoalcohol after reduction was determined by HPLC equipped with CHIRALPAK IA column ($^i$PrOH:hexane=1:10) (1.0 mL/min, the retention time of the minor enantiomer=10.5 min, the retention time of the major enantiomer=12.2 min).

N-((2R,3R)-2,4-dimethyl-1-oxopentan-3-yl)-p-toluenesulfonamide

Example 2-3

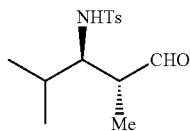

$^1$H NMR (CDCl$_3$, 400 MHz): δ 0.76 (3H, d, J=6.8 Hz), 0.77 (3H, d, J=6.8 Hz), 1.06 (3H, d, J=7.2 Hz), 1.73-1.84 (1H, m), 2.41 (3H, s), 2.66 (1H, ddq, J=1.6, 6.8, 7.2 Hz), 3.34 (1H, ddd, J=4.4, 6.8, 9.2 Hz), 5.02 (1H, d, J=9.2 Hz), 7.28 (2H, d, J=8.0 Hz), 7.74 (2H, d, J=8.0 Hz), 9.57 (1H, s);

$^{13}$C NMR (CDCl$_3$, 100 MHz): δ 11.5, 18.8, 20.2, 21.5, 30.9, 48.7, 61.0, 126.9, 129.6, 138.6, 143.3, 203.6;

IR (neat): ν 3290, 2967, 1719, 1326, 1160, 1092, 815, 667, 549 cm$^{-1}$;

HRMS (ESI): [M+Na] calculated for ([C$_{14}$H$_{21}$NNaO$_3$S]): 306.1134. found 306.1146;

[α]$_D^{21°}$ C. +32.7 (c 1.33, CHCl$_3$);

The enantiomeric excess of the corresponding amidoalcohol after reduction was determined by HPLC equipped with CHIRALPAK IA column ($^i$PrOH:hexane=1:10) (1.0 mL/min, the retention time of the minor enantiomer=12.1 min, the retention time of the major enantiomer=22.5 min).

N-((2R,3R)-2,4-dimethyl-1-oxopentan-3-yl)-p-toluenesulfonamide

Example 2-4

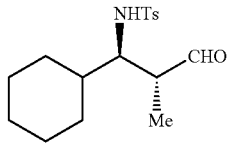

$^1$H NMR (CDCl$_3$, 400 MHz): δ 0.68-0.87 (2H, m), 0.95-1.15 (6H, In), 1.33-1.47 (2H, m), 1.53-1.70 (4H, m), 2.41 (3H, s), 2.66 (1H, dq, J=1.2, 4.0 Hz), 3.36 (1H, ddd, J=4.0, 7.2, 9.2 Hz), 5.07 (1H, d, J=9.2 Hz), 7.27 (2H, d, J=8.4 Hz), 7.73 (2H, d, J=8.4 Hz), 9.55 (1H, s);

$^{13}$C NMR (CDCl$_3$, 100 MHz): δ 11.2, 21.5, 25.9, 26.0, 26.1, 29.4, 30.6, 40.6, 48.4, 60.3, 126.9, 129.5, 138.6, 143.2, 203.6;

IR (neat): ν 3289, 2928, 2853, 1721, 1448, 1326, 1160, 1092, 815, 667 cm$^{-1}$;

HRMS (ESI): [M+Na] calculated for ([C$_{17}$H$_{25}$NNaO$_3$S]): 346.1447. found 346.1451;

[α]$_D^{22°}$ C. +24.8 (c 0.36, CHCl$_3$);

The enantiomeric excess of the corresponding amidoalcohol after reduction was determined by HPLC equipped with CHIRALPAK AD-H column ($^i$PrOH:hexane=1:10) (1.0 mL/min, the retention time of the minor enantiomer=13.7 min, the retention time of the major enantiomer=14.9 min).

N-((2R,3R)-2-methyl-1-oxo-4-phenylbutan-3-yl)-p-toluenesulfonamide

Example 2-5

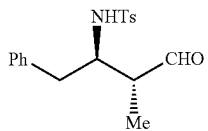

$^1$H NMR (CDCl$_3$, 400 MHz): δ 1.18 (3H, d, J=7.6 Hz), 2.40 (3H, s), 2.57 (1H, dd, J=7.2, 13.6 Hz), 2.68-2.77 (3H, m), 3.70 (1H, dq, J=3.6, 8.0 Hz), 5.03 (1H, d, J=8.0 Hz), 6.90-6.97 (2H, m), 7.14-7.22 (5H, m), 7.58 (2H, d, J=8.4 Hz), 9.57 (1H, s);

$^{13}$C NMR (CDCl$_3$, 100 MHz): δ 10.2, 21.5, 38.6, 48.3, 56.1, 126.8, 126.9, 128.7, 129.0, 129.6, 136.9, 137.4, 143.2, 203.4;

IR (neat): ν 3285, 2925, 1719, 1456, 1328, 1159, 1092, 701, 666, 550 cm$^{-1}$;

HRMS (ESI): [M+Na] calculated for ([C$_{18}$H$_{20}$NNaO$_3$S]): 330.1147. found 330.1158;

$[α]_D^{22°}$ C. +74.9 (c 0.33, CHCl$_3$);

The enantiomeric excess of the corresponding amidoalcohol after reduction was determined by HPLC equipped with CHIRALPAK IA column ($^i$PrOH:hexane=1:10) (1.0 mL/min, the retention time of the minor enantiomer=14.8 min, the retention time of the major enantiomer=16.5 min).

N-((2R,3S)-4-benzyloxy-2-methyl-1-oxobutan-3-yl)-p-toluenesulfonamide

Example 2-6

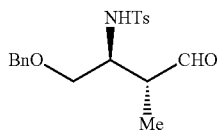

$^1$H NMR (CDCl$_3$, 400 MHz): δ 1.05 (3H, d, J=7.2 Hz), 2.41 (3H, s), 2.70-2.78 (1H, m), 3.27 (1H, dd, J=5.6, 9.6 Hz), 3.36 (1H, dd, J=4.0, 9.6 Hz), 3.61-3.68 (1H, m), 4.32 (2H, s), 5.23 (1H, br-d, J=8.8 Hz), 7.18 (2H, d, J=7.2 Hz), 7.24 (2H, d, J=8.4 Hz), 7.28-7.37 (3H, m), 7.71 (2H, d, J=8.0 Hz), 9.58 (1H, d, J=1.2 Hz);

$^{13}$C NMR (CDCl$_3$, 100 MHz): δ 10.6, 21.5, 47.6, 54.2, 69.1, 73.3, 127.0, 127.7, 128.0, 128.5, 129.7, 137.2, 137.7, 143.5, 202.6;

IR (neat): ν 3278, 2979, 2927, 2871, 1723, 1454, 1332, 1162, 1092, 826, 700, 667 cm$^{-1}$;

HRMS (ESI): [M+Na] calculated for ([C$_{19}$H$_{23}$NNaO$_4$S]): 384.1240. found 384.1244;

$[α]_D^{22°}$ C. -13.3 (c 0.34, CHCl$_3$);

The enantiomeric excess of the corresponding amidoalcohol after reduction was determined by HPLC equipped with CHIRALCEL OJ-H column ($^i$PrOH:hexane=1:10) (1.0 mL/min, anti isomer: the retention time of the minor enantiomer=49.7 min, the retention time of the major enantiomer=32.5 min, syn isomer: the retention time of the minor enantiomer=26.8 min, the retention time of the major enantiomer=40.7 min).

N-(2R,3R)-2-ethyl-1-oxo-5-phenylpentan-3-yl)-p-toluenesulfonamide

Example 2-7

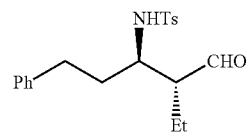

$^1$H NMR (CDCl$_3$, 400 MHz): δ 0.92 (3H, t, J=7.6 Hz), 1.42-1.54 (1H, m), 1.60-1.81 (3H, m), 2.30-2.50 (5H, m), 3.52-3.60 (1H, m), 5.07 (1H, br-d, J=9.6 Hz), 6.96 (2H, d, J=7.2 Hz), 7.12-7.33 (5H, m), 7.73 (2H, d, J=8.0 Hz), 9.56 (1H, s);

$^{13}$C NMR (CDCl$_3$, 100 MHz): δ 12.1, 18.9, 21.5, 32.3, 35.0, 52.8, 56.3, 126.1, 127.0, 128.2, 128.4, 129.7, 138.3, 140.6, 143.4, 203.7;

IR (neat): ν 3280, 2963, 2933, 2875, 1718, 1455, 1328, 1160, 1092, 816, 701, 666 cm$^{-1}$;

HRMS (ESI): [M+Na] calculated for ([C$_{20}$H$_{25}$NNaO$_3$S]): 382.1447. found 382.1429;

$[α]_D^{23°}$ C. +36.7 (c 1.45, CHCl$_3$);

The enantiomeric excess of the corresponding amidoalcohol after reduction was determined by HPLC equipped with CHIRALPAK IA column ($^i$PrOH:hexane=1:10) (1.0 mL/min, the retention time of the minor enantiomer=12.7 min, the retention time of the major enantiomer=26.5 min).

N-((1R,2R)-3-cyclohexyl-3-hydroxy-2-methylpropan-1-yl)-p-nitrobenzenesulfonamide Example 2-8

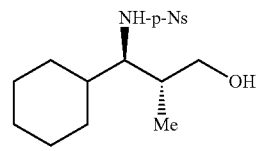

$^1$H NMR (CDCl$_3$, 400 MHz): δ 0.69-0.85 (2H, m), 0.90 (3H, t, J=6.8 Hz), 0.95-1.20 (3H, m), 1.35-1.53 (2H, m), 1.55-1.74 (5H, m), 1.76-1.87 (1H, m), 3.19 (1H, dt, J=9.2, 6.4 Hz), 3.51 (1H, dd, J=3.6, 11.2 Hz), 3.89 (1H, dd, J=3.2, 11.2 Hz), 5.39 (1H, br-d, J=9.2 Hz), 8.04 (2H, d, J=8.8 Hz), 8.33 (2H, d, J=8.8 Hz);

$^{13}$C NMR (CDCl$_3$, 100 MHz): δ 15.8, 26.1, 26.2, 28.5, 31.0, 35.7, 40.5, 63.2, 64.7, 124.1, 128.1, 147.8, 149.7;

IR (neat): ν 3526, 3303, 2929, 2854, 1530, 1449, 1350, 1309, 1162, 1092, 854, 738 cm$^{-1}$;

HRMS (ESI): [M+Na] calculated for ([C$_{16}$H$_{24}$N$_2$O$_5$SNa]): 379.1298. found 379.1302; $[α]_D^{25°}$ C. -0.3 (c 0.78, CHCl$_3$);

The enantiomeric excess was determined by HPLC equipped with CHIRALPAK AD-H column ($^i$PrOH:hexane=1:10) (1.0 mL/min, the retention time of the minor enantiomer=22.7 min, the retention time of the major enantiomer=31.5 min).

N-((1R,2R)-2-benzyloxy-1-cyclohexyl-3-hydroxypropan-1-yl)-p-nitrobenzenesulfonamide Example 2-9

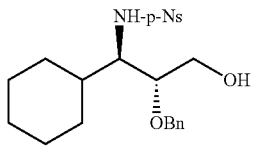

$^1$H NMR (CDCl$_3$, 400 MHz): δ 0.86-1.05 (2H, m), 1.16-1.22 (3H, m), 1.42-1.58 (2H, m), 1.59-1.70 (2H, m), 1.71-1.78 (1H, m), 1.87 (1H, br-d, J=12.8 Hz), 3.43 (1H, dt, J=4.8, 3.2 Hz), 3.56 (1H, ddd, J=4.8, 7.2, 9.2 Hz), 3.75 (1H, dd, J=3.2, 12.4 Hz), 3.81 (1H, dd, J=3.2, 12.4 Hz), 4.33 (1H, d, J=11.6 Hz), 4.37 (1H, d, J=11.6 Hz), 5.62 (1H, d, J=9.2 Hz), 7.13 (2H, dd, J=2.8, 7.2 Hz), 7.25-7.30 (3H, m), 7.95 (2H, br-d, J=8.8 Hz), 8.10 (2H, br-d, J=8.8 Hz);

$^{13}$C NMR (CDCl$_3$, 100 MHz): δ 25.9, 26.01, 26.04, 29.2, 30.7, 39.5, 60.8, 60.9, 71.5, 77.3, 123.8, 127.7, 128.0, 128.1, 128.5, 137.3, 147.6, 149.4;

[α]$_D$$^{25°}$ C. −37.5 (c 0.35, CHCl$_3$);

IR (neat): ν 3524, 3298, 2928, 2854, 1529, 1452, 1349, 1310, 1162, 1093, 854, 738 cm$^{-1}$;

HRMS (ESI): [M+Na] calculated for ([C$_{22}$H$_{28}$N$_2$O$_6$SNa]): 471.1560. found 471.1550; The enantiomeric excess was determined by HPLC equipped with CHIRALPAK IC column ($^i$PrOH:hexane=1:10) (1.0 mL/min, the retention time of the minor enantiomer=42.6 min, the retention time of the major enantiomer=34.8 min).

N-((2R,3S)-2-methyl-1-oxo-3-phenylpropan-3-yl)-p-toluenesulfonamide

Example 2-10

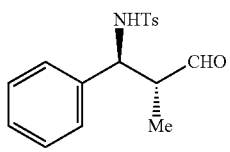

$^1$H NMR (CDCl$_3$, 400 MHz): δ 0.98 (3H, d, J=7.2 Hz), 2.32 (3H, s), 2.80 (1H, d of quint, J=2.4, 7.2 Hz), 4.54 (1H, t, J=8.4 Hz), 5.74 (1H, d, J=8.8 Hz), 6.96-7.02 (2H, m), 7.05 (2H, d, J=8.4 Hz), 7.09-7.15 (3H, m), 7.47 (2H, d, J=8.0 Hz), 9.62 (1H, d, J=2.4 Hz);

$^{13}$C NMR (CDCl$_3$, 100 MHz): δ 11.8, 21.4, 51.9, 59.1, 126.9, 127.0, 127.7, 128.5, 129.2, 137.3, 138.0, 143.1, 203.1;

IR (neat): ν 3263, 2974, 2931, 2874, 2712, 1731, 1457, 1322, 1158, 1091, 913, 703, 671, 566 cm$^{-1}$.

The enantiomeric excess was determined by HPLC equipped with CHIRALPAK AS-H column ($^i$PrOH:hexane=1:10) (1.0 mL/min, the retention time of the minor enantiomer=15.4 min, the retention time of the major enantiomer=23.3 min).

N-((1S,2R)-3-hydroxy-2-methyl-1-phenylpropan-1-yl)-p-toluenesulfonamide

Example 2-11

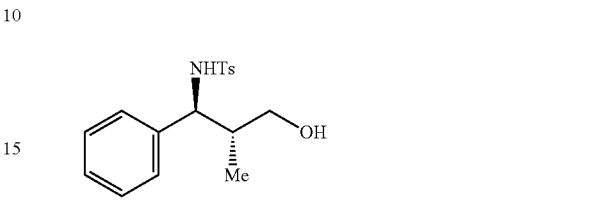

$^1$H NMR (CDCl$_3$, 400 MHz): δ 0.78 (3H, d, J=7.2 Hz), 1.88-2.00 (1H, m), 2.27 (1H, br-s), 2.34 (3H, s,), 3.55 (1H, dd, J=4.4, 11.2 Hz), 3.93 (1H, dd, J=3.2, 11.2 Hz), 4.18 (1H, t, J=8.4 Hz), 5.77 (1H, br-d, J=7.6 Hz), 6.91-6.96 (2H, m), 7.08 (2H, d, J=8.4 Hz), 7.10-7.15 (3H, m), 7.48 (2H, br-d, J=8.2 Hz);

$^{13}$C NMR (CDCl$_3$, 100 MHz): δ 14.5, 21.4, 40.9, 61.5, 64.9, 126.8, 127.1, 127.3, 128.3, 129.2, 137.4, 140.1, 143.0;

IR (neat): ν 3509, 3280, 2925, 1600, 1456, 1158, 1092, 1030, 812, 703, 669 cm$^{-1}$;

HRMS (ESI): [M+Na] calculated for ([C$_{17}$H$_{21}$NO$_3$SNa]): 342.1134. found 342.1148;

[α]$_D$$^{26°}$ C. −39.5 (c 0.52, CHCl$_3$);

The enantiomeric excess was determined by HPLC equipped with CHIRALPAK AS-H column ($^i$PrOH:hexane=1:10) (1.0 mL/min, the retention time of the minor enantiomer=15.4 min, the retention time of the major enantiomer=23.3 min).

N-((1S,2R)-3-hydroxy-1-(p-methoxyphenyl)-2-methylpropan-1-yl)-p-toluenesulfonamide Example 2-12

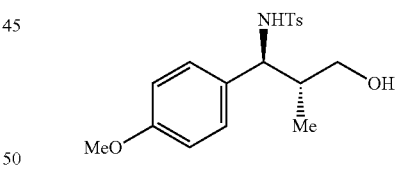

$^1$H NMR (CDCl$_3$, 400 MHz): δ 0.75 (3H, d, J=6.8 Hz), 1.86-1.92 (1H, m), 2.35 (3H, s), 3.55 (1H, dd, J=4.4, 11.2 Hz), 3.74 (3H, s), 3.93 (1H, dd, J=3.2, 11.2 Hz), 4.13 (1H, t, J=8.0 Hz), 5.70 (1H, br-d, J=7.6 Hz), 6.65 (2H, br-d, J=8.8 Hz), 6.84 (2H, br-d, J=8.8 Hz), 7.10 (2H, d, J=8.0 Hz), 7.49 (2H, d, J=8.4 Hz);

$^{13}$C NMR (CDCl$_3$, 100 MHz): δ 14.5, 21.4, 41.0, 55.2, 61.0, 65.0, 113.7, 127.1, 128.0, 129.2, 132.2, 137.5, 142.9, 158.8;

IR (neat): ν 3734, 3522, 2962, 2932, 1613, 1514, 1456, 1319, 1248, 1157, 1034, 814, 667 cm$^{-1}$;

HRMS (ESI): [M+Na] calculated for ([C$_{18}$H$_{23}$NO$_4$SNa]): 372.1240. found 372.1239;

[α]$_D$$^{27°}$ C. −53.5 (c 0.81, CHCl$_3$);

The enantiomeric excess was determined by HPLC equipped with CHIRALPAK AS-H column ($^i$PrOH:hexane=1:10) (1.0 mL/min, the retention time of the minor enantiomer=23.2 min, the retention time of the major enantiomer=52.6 min).

N-((1S,2R)-1-(p-bromophenyl)-3-hydroxy-2-methyl-propan-1-yl)-p-toluenesulfonamide Example 2-13

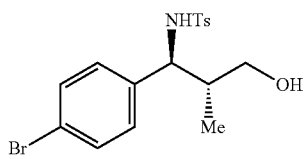

$^1$H NMR (CDCl$_3$, 400 MHz): δ 0.75 (3H, d, J=6.8 Hz), 1.85-1.96 (1H, m), 2.37 (3H, s), 2.46 (1H, br-s), 3.55 (1H, dt, J=11.2, 4.8 Hz), 3.83 (1H, dt, J=11.2, 3.6 Hz), 4.18 (1H, t, J=8.0 Hz), 6.31 (1H, br-d, J=7.2 Hz), 6.86 (2H, d, J=8.0 Hz), 7.10 (2H, d, J=8.0 Hz), 7.22 (2H, d, J=8.4 Hz), 7.47 (2H, d, J=8.4 Hz);

$^{13}$C NMR (CDCl$_3$, 100 MHz): δ 14.4, 21.4, 40.5, 61.4, 65.1, 121.1, 127.0, 128.8, 129.3, 131.3, 137.3, 139.1, 143.2;

IR (neat): ν 3488, 3274, 2964, 2927, 2883, 1597, 1489, 1456, 1322, 1158, 1092, 813, 661, 570 cm$^{-1}$;

HRMS (ESI): [M+Na] calculated for ([C$_{17}$H$_{20}$BrNO$_3$SNa]): 420.0239. found 420.0225; [α]$_D^{26°}$ C. −54.4 (c 0.36, CHCl$_3$);

The enantiomeric excess was determined by HPLC equipped with CHIRALPAK AS-H column ($^i$PrOH:hexane=1:10) (1.0 mL/min, the retention time of the minor enantiomer=14.9 min, the retention time of the major enantiomer=27.6 min).

N-((1S,2R)-3-hydroxy-2-methyl-1-(p-trifluoromethylphenyl)propan-1-yl)-p-toluenesulfonamide Example 2-14

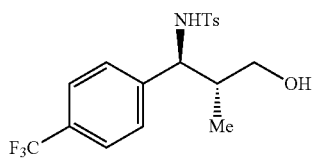

$^1$H NMR (CDCl$_3$, 400 MHz): δ 0.80 (3H, d, J=6.8 Hz), 1.90-2.01 (1H, m), 2.24 (1H, t, J=4.8 Hz), 2.32 (3H, s), 3.57 (1H, dt, J=10.8, 5.6 Hz), 3.82 (1H, dt, J=10.8, 3.2 Hz), 4.32 (1H, t, J=7.6 Hz), 6.32 (1H, br-d, J=6.8 Hz), 7.05 (2H, d, J=8.0 Hz), 7.12 (2H, d, J=8.0 Hz), 7.35 (2H, d, J=8.0 Hz), 7.44 (8.4 Hz);

$^{13}$C NMR (CDCl$_3$, 100 MHz): δ 14.5, 21.2, 40.4, 61.7, 65.2, 124.0 (q, J=270.0 Hz), 125.0 (q, J=4.0 Hz), 127.0, 127.6, 129.2, 129.3 (q, J=32.0 Hz), 137.2, 143.2, 143.9;

IR (neat): ν 3459, 3178, 2927, 1619, 1599, 1455, 1421, 1161, 1067, 1043, 814 cm$^{-1}$;

HRMS (ESI): [M+Na] calculated for ([C$_{18}$H$_{20}$F$_3$NO$_3$SNa]): 410.1008. found 410.1001 [α]$_D^{26°}$ C. −33.3 (c 0.36, CHCl$_3$);

The enantiomeric excess was determined by HPLC equipped with CHIRALPAK AS-H column ($^i$PrOH:hexane=1:10) (1.0 mL/min, the retention time of the minor enantiomer=10.0 min, the retention time of the major enantiomer=20.8 min).

TABLE 2

| Example | Product | Saturated Brine | | | 1,4-Dioxane | | |
|---|---|---|---|---|---|---|---|
| | | Yield (%) | anti:syn | ee (%) | Yield (%) | anti:syn | ee (%) |
| 2-1 | (structure) | 76 | 84:16 | 94 | 79 | 88:12 | 96 |
| 2-2 | (structure) | 61 | 89:11 | 97 | 71 | >95:5 | 99 |
| 2-3 | (structure) | 67 | 91:9 | 98 | 71 | 88:12 | 98 |

TABLE 2-continued

| Example | Product | Saturated Brine | | | 1,4-Dioxane | | |
|---|---|---|---|---|---|---|---|
| | | Yield (%) | anti:syn | ee (%) | Yield (%) | anti:syn | ee (%) |
| 2-4 | Cyclohexyl-CH(NHTs)-CH(Me)-CHO | 72 | >95:5 | 95 | 71 | >95:5 | 94 |
| 2-5 | PhCH2-CH(NHTs)-CH(Me)-CHO | 68 | >95:5 | 95 | 35 | 86:14 | 96 |
| 2-6 | BnOCH2-CH(NHTs)-CH(Me)-CHO | 77 | 77:23 | 96 | 53 | 78:22 | 90 |
| 2-7 | Ph(CH2)2-CH(NHTs)-CH(Et)-CHO | 28 | 90:10 | 98 | 77 | 93:7 | 99 |
| 2-8 | Cyclohexyl-CH(NHNs)-CH(Me)-CH2OH | 52 | >95:5 | 97 | 69 | >95:5 | 98 |
| 2-9 | Cyclohexyl-CH(NHNs)-CH(OBn)-CH2OH | 9 | >95:5 | 95 | 74 | >95:5 | 98 |
| 2-10 | Ph-CH(NHTs)-CH(Me)-CHO | 88 | 72:28 | 92 | 87 | 78:22 | 99 |
| 2-11 | Ph-CH(NHTs)-CH(Me)-CH2OH | quant. | 78:22 | 92 | 88 | 78:22 | 98 |
| 2-12 | 4-MeO-C6H4-CH(NHTs)-CH(Me)-CH2OH | 65 | 71:29 | 84 | quant. | 77:23 | 98 |

TABLE 2-continued

| Example | Product | Saturated Brine | | | 1,4-Dioxane | | |
|---|---|---|---|---|---|---|---|
| | | Yield (%) | anti:syn | ee (%) | Yield (%) | anti:syn | ee (%) |
| 2-13 | | 73 | 74:26 | 96 | 86 | 77:23 | 98 |
| 2-14 | | 84 | 72:28 | 86 | 84 | 76:24 | 99 |

Reference Example 2

Reduction Reaction

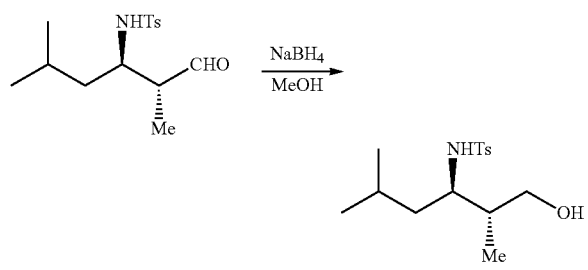

To a solution of N-((2R,3R)-2,4-dimethyl-1-oxopentan-3-yl)-p-toluenesulfonamide (30.0 mg, 0.1 mmol) in methanol (0.3 mL) was added sodium borohydride (37.8 mg, 1.0 mmol) at 0° C. The reaction mixture was stirred for 1 hr, and the reaction was quenched by addition of phosphoric acid buffer (pH 7). The reaction mixture was extracted with chloroform (3×10 mL), and the combined organic layer were dried over $Na_2SO_4$, filtered, and concentrated under reduced pressure. The residue was purified by preparative thin layer chromatography (hexane:EtOAc=2:1) to give N-((2R,3R)-2,5-dimethyl-1-hydroxyhexan-3-yl)-p-toluenesulfonamide (yield, 95%).

$^1$H NMR ($CDCl_3$, 400 MHz): δ 0.66 (3H, d, J=6.8 Hz), 0.77 (3H, d, J=6.8 Hz), 0.87 (3H, d, J=7.2 Hz), 1.16-1.29 (2H, m), 1.30-1.43 (1H, m), 1.65-1.77 (2H, m), 1.80 (1H, br-s), 2.42 (3H, s), 3.38 (1H, tt, J=5.2, 8.0 Hz), 3.46 (1H, dd, J=5.2, 10.8 Hz), 3.77 (1H, dd, J=4.0, 11.2 Hz), 4.93 (1H, d, J=8.4 Hz), 7.28 (2H, d, J=8.4 Hz), 7.76 (2H, d, J=8.0 Hz);

$^{13}$C NMR ($CDCl_3$, 100 MHz): δ 13.6, 21.5, 21.9, 23.1, 24.3, 38.9, 42.2, 54.6, 64.6, 127.0, 129.5, 138.5, 143.1;

IR (neat): ν 3522, 3282, 2957, 1599, 1464, 1319, 1157, 1094, 1031, 815, 666, 553 $cm^{-1}$;

HRMS (ESI): [M+Na] calculated for ([$C_{15}H_{25}NNaO_3S$]): 322.1447. found 322.1453;

$[α]_D^{21°}$ C. +21.1 (c 0.96, $CHCl_3$);

INDUSTRIAL APPLICABILITY

The production method of the present invention can provide a new method capable of producing an optically active β-aminoaldehyde compound from an imine compound. In the method, optically active β-aminoaldehyde compound (3) can be easily produced.

In addition, by using optically active pyrrolidine compound (4) having a particular structure, optically active β-aminoaldehyde compound (3) can be produced in good yield, superior enantioselectivity and diastereoselectivity (when $R^2$ in aldehyde compound (2) is not a hydrogen atom).

The invention claimed is:

1. A method of producing an optically active compound of formula (3):

wherein
- $R^1$ is a $C_1$-$C_{20}$ aliphatic hydrocarbon group optionally having substituent(s) selected from the following Group G1 or a hydrogen atom,
- $R^2$ is a $C_1$-$C_{20}$ hydrocarbon group optionally having substituent(s) selected from the following Group G1, a $C_1$-$C_{12}$ alkoxy group optionally having substituent(s) selected from the following Group G1, a $C_1$-$C_{12}$ alkylthio group optionally having substituent(s) selected from the following Group G1, a protected amino group, a heterocyclic group optionally having substituent(s) selected from the following Group G2,
- $R^x$ is an amino-protecting group, and
- the carbon atom marked with ** is an asymmetric carbon atom, which comprises a step of reacting a compound of formula (1-1):

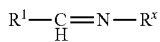

(1-1)

wherein
R¹ and R^X are as defined above,
or a compound of formula (1-2):

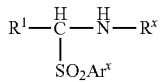

(1-2)

wherein
R¹ and R^X are as defined above, and
Ar^x is a phenyl group optionally having substituent(s) selected from the following Group G2,
with a compound of formula (2):

(2)

wherein
R² is as defined above,
in the presence of an optically active compound of formula (4):

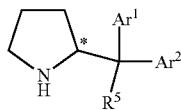

(4)

wherein
Ar¹ and Ar² are each independently a phenyl group optionally substituted by at least one $C_1$-$C_{12}$ fluorinated alkyl group,
R⁵ is a hydrogen atom, a fluorine atom, a hydroxyl group, a $C_1$-$C_{12}$ alkoxy group, a $C_1$-$C_{12}$ fluorinated alkyloxy group or —OSiR⁶R⁷R⁸ wherein R⁶, R⁷ and R⁸ are each independently a $C_1$-$C_8$ alkyl group or a $C_6$-$C_{20}$ aryl group, and the carbon atom marked with * is an asymmetric carbon atom;

<Group G1>: a group consisting of a $C_6$-$C_{20}$ aryl group optionally having substituent(s) selected from Group G2, an aromatic heterocyclic group optionally having substituent(s) selected from Group G2, a $C_1$-$C_{12}$ alkyl group, a $C_1$-$C_{12}$ alkoxy group, a $C_1$-$C_{12}$ alkyl group having $C_6$-$C_{20}$ aryl group(s) optionally having substituent(s) selected from Group G2, a $C_1$-$C_{12}$ alkoxy group having $C_6$-$C_{20}$ aryl group(s) optionally having substituent(s) selected from Group G2, a halogen atom, a $C_2$-$C_{13}$ alkylcarbonyl group, a $C_2$-$C_{13}$ alkoxycarbonyl group, a $C_1$-$C_{12}$ fluorinated alkyl group, a $C_1$-$C_{12}$ fluorinated alkyloxy group, a $C_2$-$C_{13}$ acyl group, a nitro group, a cyano group, a protected amino group and an oxo group <Group G2>: a group consisting of a $C_1$-$C_{12}$ alkyl group, a $C_1$-$C_{12}$ alkoxy group, a $C_2$-$C_{13}$ alkylcarbonyl group, a $C_2$-$C_{13}$ alkoxycarbonyl group, a $C_1$-$C_{12}$ fluorinated alkyl group, a $C_1$-$C_{12}$ fluorinated alkyloxy group, a $C_2$-$C_{13}$ acyl group, a nitro group, a cyano group, a protected amino group and a halogen atom.

2. The method of claim 1, wherein the reaction is carried out in a solvent.

3. The method of claim 2, wherein the solvent is water.

4. The method of claim 2, wherein the solvent is water containing an inorganic salt.

5. The method of claim 4, wherein the inorganic salt is sodium chloride.

6. The method of claim 2, wherein the solvent is an ether solvent.

7. The method of claim 1, wherein R⁵ is —OSiR⁶R⁷R⁸ wherein each symbol is as defined in claim 1, and Ar¹ and Ar² are each independently a phenyl group substituted with at least one $C_1$-$C_{12}$ fluorinated alkyl group.

8. The method of claim 1, wherein Ar¹ and Ar² are each independently a phenyl group optionally substituted with at least one trifluoromethyl group.

9. The method of claim 1, wherein Ar¹ and Ar² are each 3,5-bis(trifluoromethyl)phenyl.

* * * * *

UNITED STATES PATENT AND TRADEMARK OFFICE
CERTIFICATE OF CORRECTION

PATENT NO. : 8,962,889 B2
APPLICATION NO. : 13/880675
DATED : February 24, 2015
INVENTOR(S) : Hayashi It is certified that error appears in the above-identified patent and that said Letters Patent is hereby corrected as shown below:

On The Title Page:

"(22) PCT Filed: Oct. 9, 2011)" should read "(22) PCT Filed: Oct. 19, 2011)"

In The Claims:

Claim 1 at column 32, line 59, "amino group, a heterocyclic group" should read "amino group, or a heterocyclic group"

Signed and Sealed this
Sixth Day of October, 2015

Michelle K. Lee
*Director of the United States Patent and Trademark Office*